(12) United States Patent
Ray, II

(10) Patent No.: US 10,973,804 B2
(45) Date of Patent: Apr. 13, 2021

(54) COMPOSITIONS AND METHODS COMPRISING A COMPOUNDED COMPOSITION

(71) Applicant: CMPD LICENSING, LLC, Conroe, TX (US)

(72) Inventor: Jay Richard Ray, II, Conroe, TX (US)

(73) Assignee: CMPD LICENSING, LLC, Conroe, TX (US)

( * ) Notice: Subject to any disclaimer, the term of this patent is extended or adjusted under 35 U.S.C. 154(b) by 686 days.

(21) Appl. No.: 14/819,342

(22) Filed: Aug. 5, 2015

(65) Prior Publication Data

US 2017/0035736 A1 Feb. 9, 2017

(51) Int. Cl.
| | | |
|---|---|---|
| *A61K 31/496* | (2006.01) | |
| *A61K 31/4196* | (2006.01) | |
| *A61K 47/26* | (2006.01) | |
| *A61K 45/06* | (2006.01) | |
| *A61K 9/00* | (2006.01) | |
| *A61K 47/10* | (2017.01) | |

(52) U.S. Cl.
CPC ........ *A61K 31/4196* (2013.01); *A61K 9/0014* (2013.01); *A61K 45/06* (2013.01); *A61K 47/10* (2013.01); *A61K 47/26* (2013.01)

(58) Field of Classification Search
CPC .................................................. A61K 31/4196
USPC ....................................................... 514/383
See application file for complete search history.

(56) References Cited

U.S. PATENT DOCUMENTS 5,710,280 A * 1/1998 Shih ..................... C07D 231/12
548/266.6

OTHER PUBLICATIONS

PCCA XYIFOS Trademark Appl. No. 8842712 (May 27, 2015), pp. 1-8.*
Freels, Lexington Podiatry (2011), pp. 1-2.*
PCCA Loxasperse Studies (2013 and 2014, pp. 1-12.*
PCCA, publication No. 30-4701 (2013), pp. 1-2.*
Roerig, "Diflucan-fluconazole tablet, Diflucan-fluconazole powder, for suspension," Pfizer, Mar. 2013, document of 61 pages.
PCCA, "LoxaSperse™, Powder Excipient Base for Use in Nebulization and Irrigation Compounds," 2013, document of 3 pages.
Pfizer, "Fluconazole Injection, USP, in INTRAVIA Plastic Container," Pfizer Injectables, Aug. 2010, document of 4 pages, https://www.pfizer.com/files/products/uspi_fluconazole.pdf.

* cited by examiner

*Primary Examiner* — Taofiq A Solola
(74) *Attorney, Agent, or Firm* — Akerman LLP

(57) ABSTRACT

The present application relates to compounded compositions, methods of making compounded compositions, kits comprising compounded compositions, containers comprising compounded compositions, and methods of using compounded compositions. For example, disclosed herein are compounded compositions comprising an anti-fungal agent and methods of using a compounded composition to treat or prevent a fungal infection or a suspected fungal infection. This abstract is intended as a scanning tool for purposes of searching in the particular art and is not intended to be limiting of the present invention.

8 Claims, 5 Drawing Sheets

COMPOSITIONS AND METHODS COMPRISING A COMPOUNDED COMPOSITION

FIELD OF THE INVENTION

The present application relates to compounded compositions, methods of making compounded compositions, and methods of using compounded compositions. For example, disclosed herein are compounded compositions comprising an anti-fungal agent and methods of using a compounded composition to treat or prevent a fungal infection or a suspected fungal infection.

BACKGROUND OF THE INVENTION

The body normally serves as host for a variety of bacteria and fungi. Most of the time, the balance between the body as host and the microorganisms is maintained. However, there are times when the physiological, biochemical, and/or environmental conditions permit the microorganisms to tip that balance, thereby causing an infection. For example, fungi are only problematic when they grow in an uncontrolled manner, which causes various diseases and discomfort for the infected subject (e.g., a human subject or an animal subject). Unfortunately, uncontrolled fungal growths regularly occur.

Certain fungal infections of the skin known as tinea infections are caused by dermatophytes, which are members of the *Trichophyton, Microsporum*, and *Epidermophyton* species. These mold-like fungi thrive in warm, moist areas, thriving on the dead tissues of hair, nails, and outer skin layers. Tinea infections include tinea pedis, known as athlete's foot; tinea corporis, known as ringworm; tinea capitis, a fungal infection of the scalp that can cause hair loss; tinea cruris, known as jock itch or tinea of the groin; tinea unguum, which is tinea of the nails; and tinea *versicolor*, a superficial fungal infection that produces brown, tan, or white spots on the trunk of the body. Tinea infections are contagious and can be passed through direct contact or by contact with clothing, from shower and pool surfaces, and even from pets.

Athlete's foot or tinea pedis is by far the most common form, with more than 12 million people in the United States suffering from the disease per year. It presents with redness, itching, burning, cracking, scaling, swelling, and occasionally bleeding. Athlete's foot includes toe web infections, moccasin type infections, and vesicular type infections. The condition generally includes small vesicles, fissures, scaling, maceration, hyperkeratinization, and eroded areas between the toes and on the plantar surface of the foot, as well as on other skin areas. For example, the nails may show thickening, pitting, and subungal debris.

Reoccurrences of the infection are frequent. For some subjects, such as those also diagnosed with diabetes or circulatory problems, or obese subjects, tinea infections and their treatment can be quite serious. The source of the affliction often is a public safety and health concern, as the occurrence of tinea pedis is higher in public areas such as locker rooms, public showers, sports facilities, and the like.

Moreover, there are at least 3 different types of nail infections caused by fungi. The most common infection is frequently caused by *Trichophyton rubrum* and affects the nail bed and the area beneath the nail. Another type of infection affects only the nail surface and creates white or light colored patches. This second type of fungal infection is unusual and represents only about 10% of the reported cases.

A third type of fungal infection affects the nail root and usually afflicts persons with impaired immune defense. A fourth (and unusual) type is caused by an infection of yeast fungi. Infections by yeast most often only affect nails that already are infected or damaged in some way.

The fungi are invasive to the keratin nail tissue. Apart from becoming discolored and brittle, the nail may often separate from the nail bed. In addition, pain and difficulty in wearing foot apparel is often experienced. Initially, the disease affects only one nail, typically one nail of the foot, and is thereafter spread to more nails. The palms of the hands and the soles of the feet may frequently be affected as well. When the skin is affected, red spots frequently occur and the skin may peel off. Nail fungal infections are one of the hardest forms of external infection to treat, of which infections of toe nails are the most difficult to treat.

Despite advances in the understanding of the pathology of fungal infections, especially fungal infections that affect a subject's appendages (such as one foot or both feet), there is still a need for compositions and methods that efficiently treat or prevent the progression and reoccurrence of fungal infections.

BRIEF SUMMARY OF THE INVENTION

Disclosed herein is a compounded composition comprising an anti-infective agent and an excipient base powder comprising a blend of micronized xylitol and poloxamers.

Disclosed herein is a compounded composition comprising an anti-fungal agent and an excipient base powder comprising a blend of micronized xylitol and poloxamers.

Disclosed herein is a compounded composition, comprising fluconazole and an excipient base powder comprising a blend of micronized xylitol and poloxamers Disclosed herein is a compounded composition, comprising itraconazole, voriconazole, or a combination thereof, and an excipient base powder comprising a blend of micronized xylitol and poloxamers.

Disclosed herein is a compounded composition comprising an anti-fungal agent, an excipient base powder comprising a blend of micronized xylitol and poloxamers, and one or more additional anti-infective agents.

Disclosed herein is a compounded composition for treating or preventing a fungal infection using a foot bath, the compounded composition comprising fluconazole and an excipient base powder comprising a blend of micronized xylitol and poloxamers.

Disclosed herein is a kit, comprising: a container comprising a compounded composition, wherein the compounded composition comprises a therapeutically effective amount of an anti-fungal agent and a sufficient amount of an excipient base powder comprising a blend of micronized xylitol and poloxamers.

Disclosed herein is a kit, comprising: a container comprising a compounded composition, wherein the compounded composition comprises a therapeutically effective amount of an anti-fungal agent and a sufficient amount of an excipient base powder comprising a blend of micronized xylitol and poloxamers, and instructions for using the compounded composition.

Disclosed herein is a kit, comprising: a container comprising a compounded composition, wherein the compounded composition comprises a therapeutically effective amount of an anti-fungal agent, a therapeutically effective amount of an anti-infective agent, and a sufficient amount of an excipient base powder comprising a blend of micronized xylitol and poloxamers, and instructions for using the compounded composition.

Disclosed herein is a kit, comprising: a container comprising a compounded composition, wherein the compounded composition comprises a therapeutically effective amount of an anti-fungal agent and a sufficient amount of an excipient base powder comprising a blend of micronized xylitol and poloxamers, a foot bath, and instructions for using the compounded composition.

Disclosed herein is a kit, comprising: a container comprising an anti-fungal agent, a container comprising an excipient base powder comprising a blend of micronized xylitol and poloxamers, and instructions for using the anti-fungal agent and the excipient base powder.

Disclosed herein is a kit, comprising: a container comprising an anti-fungal agent, a container comprising an excipient base powder comprising a blend of micronized xylitol and poloxamers, instructions for making a compounded composition comprising a therapeutically effective amount of the anti-fungal agent and a sufficient amount of the excipient base powder, and instructions for using the compounded composition.

Disclosed herein is a kit, comprising: a container comprising an anti-fungal agent, a container comprising an excipient base powder comprising a blend of micronized xylitol and poloxamers, instructions for making a compounded composition comprising a therapeutically effective amount of the anti-fungal agent and a sufficient amount of the excipient base powder, a foot bath, and instructions for using the compounded composition.

Disclosed herein is a kit, comprising: a container comprising an anti-fungal agent, a container comprising an anti-infective agent, a container comprising an excipient base powder comprising a blend of micronized xylitol and poloxamers, instructions for making a compounded composition comprising a therapeutically effective amount of the anti-fungal agent, a therapeutically effective amount of the anti-infective agent, and a sufficient amount of the excipient base powder, a foot bath, and instructions for using the compounded composition.

Disclosed herein is a kit, comprising: a container comprising a compounded composition, wherein the compounded composition comprises a therapeutically effective amount of fluconazole and a sufficient amount of an excipient base powder comprising a blend of micronized xylitol and poloxamers, and instructions for using the compounded composition.

Disclosed herein is a kit, comprising: a container comprising a compounded composition, wherein the compounded composition comprises a therapeutically effective amount of fluconazole, a therapeutically effective amount of an anti-infective agent, and a sufficient amount of an excipient base powder comprising a blend of micronized xylitol and poloxamers, and instructions for using the compounded composition.

Disclosed herein is a kit, comprising: a container comprising a compounded composition, wherein the compounded composition comprises a therapeutically effective amount of fluconazole and a sufficient amount of an excipient base powder comprising a blend of micronized xylitol and poloxamers, a foot bath, and instructions for using the compounded composition.

Disclosed herein is a kit, comprising: a container comprising fluconazole, a container comprising an excipient base powder comprising a blend of micronized xylitol and poloxamers, and instructions for using the anti-fungal agent and the excipient base powder.

Disclosed herein is a kit, comprising: a container comprising fluconazole, a container comprising an excipient base powder comprising a blend of micronized xylitol and poloxamers, instructions for making a compounded composition comprising a therapeutically effective amount of the anti-fungal agent and a sufficient amount of the excipient base powder, and instructions for using the compounded composition.

Disclosed herein is a kit, comprising: a container comprising fluconazole, a container comprising an excipient base powder comprising a blend of micronized xylitol and poloxamers, instructions for making a compounded composition comprising a therapeutically effective amount of fluconazole and a sufficient amount of the excipient base powder, a foot bath, and instructions for using the compounded composition.

Disclosed herein is a method of treating or preventing a fungal infection, the method comprising: (i) adding a compounded composition to water contained within a foot bath; (ii) agitating the water contained within the foot bath; and (iii) contacting the agitated water with at least a portion of one or both feet of a subject.

Disclosed herein is a method of treating or preventing a fungal infection, the method comprising: (i) adding to water contained within a foot bath a compounded composition comprising an anti-fungal agent and an excipient base powder comprising a blend a micronized xylitol and poloxamers; (ii) agitating the water contained within the foot bath; and (iii) contacting the agitated water with at least a portion of one or both feet of a subject.

Disclosed herein is a method of treating or preventing a fungal infection, the method comprising: (i) adding to water contained within a foot bath a compounded composition comprising an anti-fungal agent, one or more additional anti-infective agents, and an excipient base powder comprising a blend a micronized xylitol and poloxamers; (ii) agitating the water contained within the foot bath; and (iii) contacting the agitated water with at least a portion of one or both feet of a subject.

Disclosed herein is a method of treating or preventing a fungal infection in a subject, the method comprising: (i) adding to water contained within a foot bath a compounded composition comprising fluconazole and LoxaSperse™ excipient base powder; (ii) agitating the water using an agitator, thereby distributing the compounded composition throughout the water; and (iii) contacting the agitated water with at least a portion of one or both feet of a subject, wherein the subject has been diagnosed with, is suspected of having, or is at risk of developing a fungal infection.

Disclosed herein is a method of treating or preventing a fungal infection, the method comprising: (i) adding to water contained within a foot bath a compounded composition comprising an anti-fungal agent and an excipient base powder comprising a blend of micronized xylitol and poloxamers; (ii) agitating the water contained within the foot bath; and (iii) contacting the agitated water with at least a portion of one or both feet of a subject.

Disclosed herein is a method of making a compounded composition, the method comprising: mixing a therapeutically effective amount of an anti-fungal agent and a sufficient amount of an excipient base powder comprising a blend of micronized xylitol and poloxamers to make a compounded composition.

Disclosed herein is a method of making a compounded composition, the method comprising: mixing a therapeutically effective amount of an anti-fungal agent, a therapeutically effective amount of one or more additional anti-infective agents, and a sufficient amount of an excipient base powder comprising a blend of micronized xylitol and poloxamers to make a compounded composition.

Disclosed herein is a method of making a compounded composition for treating or preventing a fungal infection using a foot bath, the method comprising: obtaining an anti-fungal agent, an excipient base powder comprising a blend of micronized xylitol and poloxamers, or both; mixing a therapeutically effective amount of the anti-fungal agent and a sufficient amount of the excipient base powder to make a homogenous compounded composition.

Figure 1:
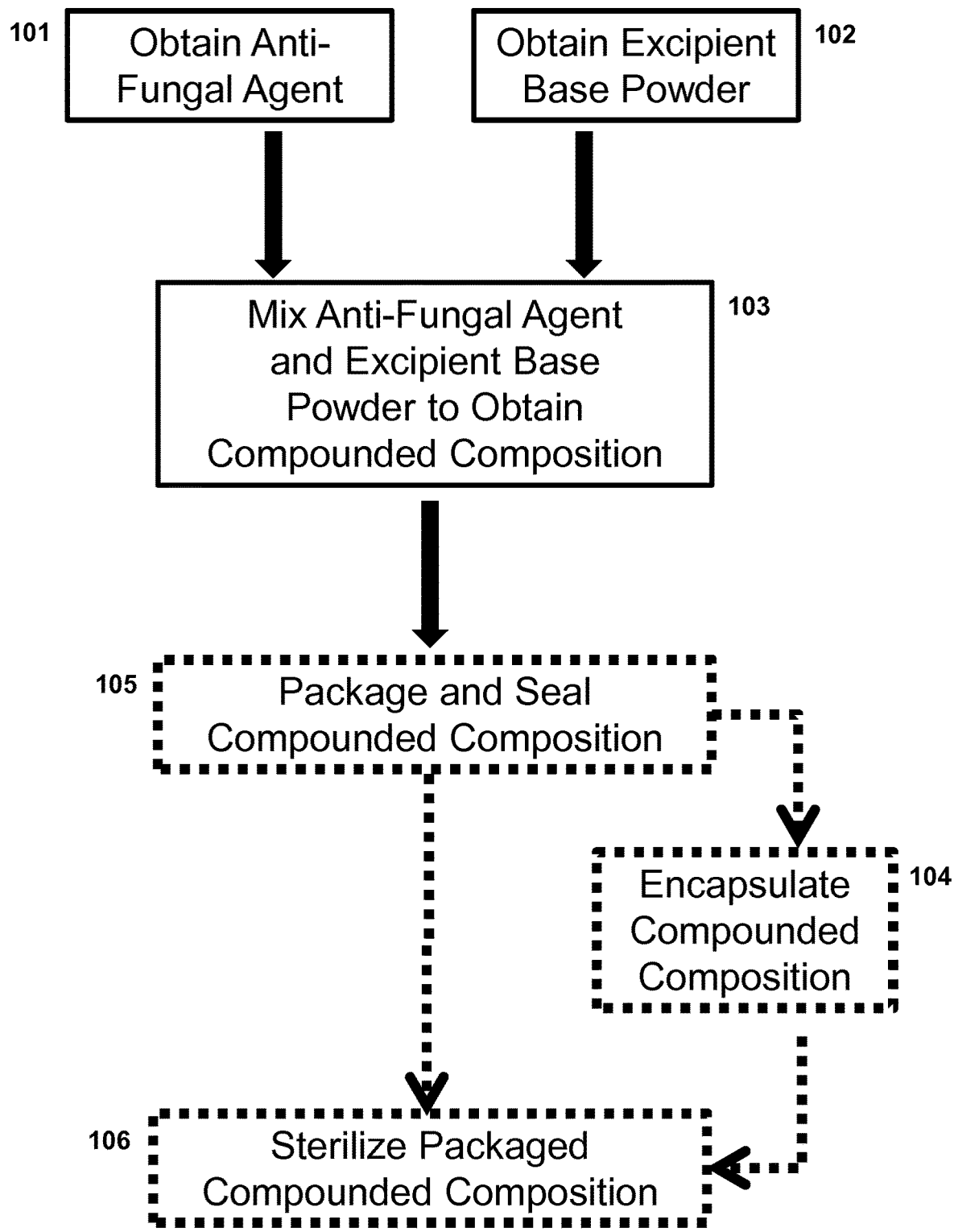
FIG. 1 shows a schematic of a disclosed method of making a compounded composition, wherein the compounded composition comprises an anti-fungal agent and an excipient base powder.

Additional advantages of the invention will be set forth in part in the description which follows, and in part will be obvious from the description, or can be learned by practice of the invention. The advantages of the invention will be realized and attained by means of the elements and combinations particularly pointed out in the appended claims. It is to be understood that both the foregoing general description and the following detailed description are exemplary and explanatory only and are not restrictive of the invention, as claimed.

DETAILED DESCRIPTION OF THE INVENTION

The present invention can be understood more readily by reference to the following detailed description of the invention and the Examples included therein.

Before the present compounds, compositions, articles, systems, devices, and/or methods are disclosed and described, it is to be understood that they are not limited to specific synthetic methods unless otherwise specified, or to particular reagents unless otherwise specified, as such may, of course, vary. It is also to be understood that the terminology used herein is for the purpose of describing particular aspects only and is not intended to be limiting. Although any methods and materials similar or equivalent to those described herein can be used in the practice or testing of the present invention, example methods and materials are now described.

All publications mentioned herein are incorporated herein by reference to disclose and describe the methods and/or materials in connection with which the publications are cited. The publications discussed herein are provided solely for their disclosure prior to the filing date of the present application. Nothing herein is to be construed as an admission that the present invention is not entitled to antedate such publication by virtue of prior invention.

A. Definitions

As used in the specification and the appended claims, the singular forms "a", "an", and "the" include plural referents unless the context clearly dictates otherwise.

The phrase "consisting essentially of" limits the scope of a claim to the recited components in a composition or the recited steps in a method as well as those that do not materially affect the basic and novel characteristic or characteristics of the claimed composition or claimed method.

The phrase "consisting of" excludes any component, step, or element that is not recited in the claim.

The phrase "comprising" is synonymous with "including", "containing", or "characterized by", and is inclusive or open-ended. "Comprising" does not exclude additional, unrecited components or steps.

As used herein when referring to any numerical value, the term "about" means a value falling within a range that is ±10% of the stated value.

Ranges can be expressed herein as from "about" one particular value, and/or to "about" another particular value. When such a range is expressed, a further aspect includes from the one particular value and/or to the other particular value. Similarly, when values are expressed as approximations, by use of the antecedent "about," it will be understood that the particular value forms a further aspect. It will be further understood that the endpoints of each of the ranges are significant both in relation to the other endpoint, and independently of the other endpoint. It is also understood that there are a number of values disclosed herein, and that each value is also herein disclosed as "about" that particular value in addition to the value itself. For example, if the value "10" is disclosed, then "about 10" is also disclosed. It is also understood that each unit between two particular units are also disclosed. For example, if 10 and 15 are disclosed, then 11, 12, 13, and 14 are also disclosed.

References in the specification and concluding claims to parts by weight of a particular element or component in a composition denotes the weight relationship between the element or component and any other elements or components in the composition or article for which a part by weight is expressed. Thus, in a compound containing 2 parts by weight of component X and 5 parts by weight component Y, X and Y are present at a weight ratio of 2:5, and are present in such ratio regardless of whether additional components are contained in the compound.

As used herein, the terms "optional" or "optionally" means that the subsequently described event or circumstance can or cannot occur, and that the description includes instances where said event or circumstance occurs and instances where it does not. For example, in an aspect, a disclosed method can optionally comprise one or more additional steps, such as, for example, repeating an administering step or altering an administering step.

As used herein, "fluconazole" refers to the first of a new subclass of synthetic triazole antifungal agents, which is designated chemically as 2,4-difluoro-α,α1-bis(1H-1,2,4-triazol-1-ylmethyl) benzyl alcohol with an empirical formula of $C_{13}H_{12}F_2N_6O$ and molecular weight 306.3. The structural formula is:

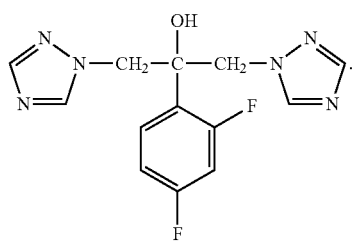 [SMILES: OC(Cn1cncn1)(Cn1cncn1)c1ccc(F)cc1F]

Fluconazole is a white crystalline solid which is slightly soluble in water and saline.

As used herein, the term "capsule" includes a soft or hard shell capsule. A capsule shell can be a unibody delivery vehicle or can be comprised of two capsule shell pieces. In an aspect, the longer capsule shell piece can be called the "body" and the smaller capsule shell piece can be called the "cap". The body and the cap can engage with each other as one shell body. As known to the art, capsule sizes can differ considering various factors that are tailored for any particular application, such as dosage amount or route of administration. Capsules can be manufactured to achieve a variety of capsule shell thicknesses. The release characteristics of a capsule can vary depending on the capsule shell thickness and composition. Standard capsule sizes are known in the art, and include, but are not limited to, the following sizes: Su07 (28 mL), 7 (24 mL), 10 (18 mL), 11 (10 mL), 12el (7.5 mL), 12 (5 mL), 13 (3.2 mL), 000 (1.37 mL), 00 (0.95 mL), 0 (0.68 mL), 1 (0.50 mL), 2 (0.37 mL), 3 (0.30 mL), 4 (0.21 mL), and 5 (0.13 mL). Actual volumes in mL are shown in parenthesis. Capsules for oral administration typically range from a size 5 (volume of 0.1 mL) capsule to a size 000 (volume of 1.37 mL) capsule. In an aspect, a disclosed compounded composition can be encapsulated in a capsule or in one or more capsules.

As used herein, the term "subject" refers to the target of administration, e.g., an animal. The term "subject" also includes domesticated animals (e.g., cats, dogs, etc.), livestock (e.g., cattle, horses, pigs, sheep, goats, etc.), and laboratory animals (e.g., mouse, rabbit, rat, guinea pig, fruit fly, etc.). Thus, the subject of the herein disclosed methods can be a vertebrate, such as a mammal, a fish, a bird, a reptile, or an amphibian. Alternatively, the subject of the herein disclosed methods can be a human, non-human primate, horse, pig, rabbit, dog, sheep, goat, cow, cat, guinea pig, or rodent. The term does not denote a particular age or sex. Thus, adult and newborn subjects, as well as fetuses, whether male or female, are intended to be covered. In an aspect, a subject can be a human patient. A subject can have diabetes. A subject can be obese. A subject can have circulatory issues. A subject can have a fungal infection, be suspected of having a fungal infection, or be at risk of developing a fungal infection.

For example, a subject at risk of developing a fungal infection can have, for example, risk factors for developing a fungal infection (e.g., have damaged or moist skin, have chronic disease, and/or be immunocompromised). For example, a subject at risk for developing a fungal infection can be exposed to a fungus due to employment (e.g., a health care worker) or due to the prevalence of a fungus at a specific location (e.g., a hospital).

A "patient" refers to a subject afflicted with one or more diseases or disorders, such as, for example, diabetes, or pre-diabetes, or a fungal infection or a suspected fungal infection, such as for example, a fungal infection or suspected fungal infection of one foot or both feet. A patient can refer to a subject that has been diagnosed with or is suspected of having a fungal infection. In an aspect, a fungal infection or suspected fungal infection can affect at least a portion of one or both feet of the subject. In an aspect, a fungal infection or suspected fungal infection can affect another appendage, such as at least a portion of one or both of the subject's hands.

As used herein, the term "treatment" refers to the medical management of a patient with the intent to cure, ameliorate, stabilize, or prevent a disease, pathological condition, or disorder (such as, for example, a fungal infection or a suspected fungal infection). This term includes active treatment, that is, treatment directed specifically toward the improvement of a disease, pathological condition, or disorder, and also includes causal treatment, that is, treatment directed toward removal of the cause of the associated disease, pathological condition, or disorder. In addition, this term includes palliative treatment, that is, treatment designed for the relief of symptoms rather than the curing of the disease, pathological condition, or disorder; preventative treatment, that is, treatment directed to minimizing or partially or completely inhibiting the development of the associated disease, pathological condition, or disorder; and supportive treatment, that is, treatment employed to supplement another specific therapy directed toward the improvement of the associated disease, pathological condition, or disorder. In various aspects, the term covers any treatment of a subject, including a mammal (e.g., a human), and includes: (i) preventing the disease from occurring in a subject that can be predisposed to the disease but has not yet been diagnosed as having it; (ii) inhibiting the disease, i.e., arresting its development; or (iii) relieving the disease, i.e., causing regression of the disease.

In an aspect, "treating" means eradicating a fungal infection or a suspected fungal infection. In an aspect, "treating" means reducing the effects of a fungal infection or symptoms of a fungal infection. Thus, in an aspect of a disclosed method, treating can refer to a 10%, 20%, 30%, 40%, 50%, 60%, 70%, 80%, 90%, or 100% reduction in the severity of an established fungal infection or symptoms of a fungal infection. For example, a method for treating a fungal infection can reduce one or more symptoms of a fungal infection in a subject by 10% as compared to a control. In an aspect, a reduction of one or more symptoms can be 20%, 30%, 40%, 50%, 60%, 70%, 80%, 90%, 100%, or any percent reduction in between 10% and 100% as compared to a control. It is understood that treatment does not necessarily refer to a cure or complete ablation or eradication of the fungal infection. However, in an aspect, treatment can refer to a cure or complete ablation or eradication of the fungal infection.

As used herein, the term "prevent" or "preventing" refers to precluding, averting, obviating, forestalling, stopping, or hindering something from happening, especially by advance action. It is understood that where reduce, inhibit or prevent are used herein, unless specifically indicated otherwise, the use of the other two words is also expressly disclosed. In an aspect, preventing a fungal infection is intended.

As used herein, the term "diagnosed" means having been subjected to a physical examination by a person of skill, for example, a physician, and found to have a condition that can be diagnosed or treated by the compounds, compositions, or methods disclosed herein. For example, "diagnosed with a fungal infection" means having been subjected to a physical examination by a person of skill, for example, a physician, and found to have a condition that can be diagnosed or can be treated by a compound or composition that can prevent or inhibit a fungal infection. For example, "suspected of having a fungal infection" can mean having been subjected to a physical examination by a person of skill, for example, a physician, and found to have a condition that can be likely be diagnosed as or can likely be treated by a compound or composition that can prevent or inhibit a fungal infection, or it can mean that the subject believes that he or she has a fungal infection.

As used herein, the terms "administering" and "administration" refer to any method of providing a disclosed composition or a disclosed compounded composition or a pharmaceutical preparation to a subject. Such methods are well known to those skilled in the art and include, but are not limited to: oral administration, transdermal administration, administration by inhalation, nasal administration, topical administration, intravaginal administration, ophthalmic administration, intraaural administration, intracerebral administration, rectal administration, sublingual administration, buccal administration, and parenteral administration, including injectable such as intravenous administration, intra-arterial administration, intramuscular administration, and subcutaneous administration. Administration can be continuous or intermittent. In various aspects, a disclosed compounded composition can be administered therapeutically; that is, administered to treat an existing disease or condition. In further various aspects, a disclosed compounded composition can be administered prophylactically; that is, administered for prevention of a disease or condition. In an aspect, the skilled person can determine an efficacious dose, an efficacious schedule, and an efficacious route of administration for a disclosed composition or a disclosed complex so as to treat a subject or inhibit or prevent an inflammatory reaction. In an aspect, the skilled person can also alter, change, or modify an aspect of an administering step so as to improve efficacy of a disclosed composition or a disclosed compounded composition. In an aspect, administering means contacting at least a portion of one foot or both feet of a subject with agitated water comprising a disclosed compounded composition in a foot bath.

As used herein, a "foot bath" refers to a container that can hold some volume (e.g., about 15 liters to about 30 liters) of aqueous solution (e.g., water) and is designed to physically accommodate at least a portion of one or both feet of a subject. Foot baths are known to the skilled person. A foot bath can comprise several features or agents that effect various functions. For example, a foot bath can comprise one or more lights or light-emitting devices, a mechanical agitation agent (e.g., one or more jets or bubble makers) to physically agitate the enclosed water, a bubble agent to create bubbles within the enclosed water, a heating agent to heat the enclosed water, a vibration agent to vibrate the enclosed water (e.g., a high frequency vibration massage), an infrared device to provide infrared light to a foot or feet of the subject, a massage agent (e.g., a roller) that provides massaging contact to at least a portion of one or both feet, a pedicure agent that can clean or contact a foot or feet with a pumice, or a combination thereof. In an aspect, an agitation agent or an agitator can be coupled to both a motor and the foot bath. Motors and agitators are known to the art. In a foot bath can comprise one or more splash guards and other spill-resistant features to ensure that the water remains enclosed within a container. A foot bath apparatus may also accommodate a subject's calves, meaning that the container is "deep" so as to allow the enclosed water to contact both the feet and at least a portion of the calves of the subject.

Several manufacturers market foot baths including MB, Dr. Scholl's, Kendal, Conair, and Brookstone.

As used herein, "modifying the method" can comprise modifying or changing one or more features or aspects of one or more steps of a disclosed method. For example, in an aspect, a method can be altered by changing the dose or the amount of a disclosed compounded composition added to a foot bath, by changing the frequency of the subject's use of the foot bath, or by changing the duration of time that the subject's foot or feet contact the water contained within the foot bath, or a combination thereof.

As used herein, poloxamers are non-ionic poly (ethylene oxide) (PEO)-poly (propylene oxide) (PPO) copolymers. Poloxamers can be used in pharmaceutical formulations as surfactants, emulsifying agents, solubilizing agent, dispersing agents, and in vivo absorbance enhancer. Poloxamers are often considered as "functional excipients" because they are essential components, and play an important role in the formulation. Poloxamers are synthetic triblock copolymers with the following formula:

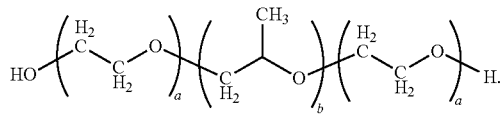

The term "contacting" as used herein refers to bringing a disclosed composition or compounded composition together with an intended target (such as at least a portion of one or both feet of a subject) or targeted area (such as an area diagnosed with, suspected of having a fungal infection, or susceptible to developing a fungal infection) in such a manner that the disclosed composition or compounded composition can exert an effect on the intended target or targeted area either directly or indirectly. In an aspect, "contacting" means to insert or immerse at least a portion of one or both feet of a subject into the water contained within a foot bath.

The term "mixing" as used in a disclosed method of making a compounded composition, for example, means to physically combine the recited components so as to achieve a homogenous compounded composition (which can be a dry powder formulation). For example, in an aspect, an anti-infective agent is mixed with an excipient base powder; that is, an anti-infective agent is physically combined with an excipient base powder and shaken, or stirred, or agitated so as to achieve a homogenous compounded composition. In an aspect, multiple recited components can be mixed together (i.e., an anti-fungal agent, an excipient base powder, and one or more additional anti-infective agents). In an aspect, "mixing" can also include sifting the homogenous compounded composition though a fine mesh strainer. A suitable mixer is a TURBUILA® mixer, which is able to mix powdery substances with differing specific weights and particle sizes. The mixing can be generally performed for a pre-determined amount of time, i.e., for 10 minutes, 20 minutes, 30 minutes, 40 minutes, 50 minutes, 1 hour, 2 hours, 3 hours, or more. A person skilled in the art could ascertain without undue experimentation, the amount of time required to mix the recited components so as to achieve a homogenous compounded composition.

The term "pharmaceutically acceptable" describes a material that is not biologically or otherwise undesirable, i.e., without causing an unacceptable level of undesirable biological effects or interacting in a deleterious manner. As used herein, the term "pharmaceutically acceptable carrier"

refers to sterile aqueous or nonaqueous solutions, dispersions, suspensions or emulsions, as well as sterile powders for reconstitution into sterile injectable solutions or dispersions just prior to use. Examples of suitable aqueous and nonaqueous carriers, diluents, solvents or vehicles include water, ethanol, polyols (such as glycerol, propylene glycol, polyethylene glycol and the like), carboxymethylcellulose and suitable mixtures thereof, vegetable oils (such as olive oil) and injectable organic esters such as ethyl oleate. These compositions can also contain adjuvants such as preservatives, wetting agents, emulsifying agents and dispersing agents. Prevention of the action of microorganisms can be ensured by the inclusion of various antibacterial and antifungal agents such as paraben, chlorobutanol, phenol, sorbic acid and the like. It can also be desirable to include isotonic agents such as sugars, sodium chloride and the like. Prolonged absorption of the injectable pharmaceutical form can be brought about by the inclusion of agents, such as aluminum monostearate and gelatin, which delay absorption. Injectable depot forms are made by forming microencapsule matrices of the drug in biodegradable polymers such as polylactide-polyglycolide, poly(orthoesters) and poly(anhydrides). Depending upon the ratio of drug to polymer and the nature of the particular polymer employed, the rate of drug release can be controlled. Depot injectable formulations are also prepared by entrapping the drug in liposomes or microemulsions which are compatible with body tissues. The injectable formulations can be sterilized, for example, by filtration through a bacterial-retaining filter or by incorporating sterilizing agents in the form of sterile solid compositions which can be dissolved or dispersed in sterile water or other sterile injectable media just prior to use. Suitable inert carriers can include sugars such as lactose.

As used herein, the term "determining" can refer to measuring or ascertaining the presence and severity of an infection, such as, for example, a fungal infection that affects one or more of a subject's appendages (e.g., at least a portion of one or both feet). Methods and techniques used to determining the presence and/or severity of an infection are typically known to the medical arts. For example, the art is familiar with the ways to identify and/or diagnose the presence, severity, or both of a fungal infection.

As used herein, the terms "effective amount" and "amount effective" can refer to an amount that is sufficient to achieve the desired result such as, for example, the treatment and/or prevention of a fungal infection or a suspected fungal infection. As used herein, the terms "effective amount" and "amount effective" can refer to an amount that is sufficient to achieve the desired an effect on an undesired condition (e.g., a fungal infection). For example, a "therapeutically effective amount" refers to an amount that is sufficient to achieve the desired therapeutic result or to have an effect on undesired symptoms, but is generally insufficient to cause adverse side effects. The specific therapeutically effective dose level for any particular patient will depend upon a variety of factors including the disorder being treated and the severity of the disorder; the specific composition employed; the age, body weight, general health, sex and diet of the patient; the time of administration; the route of administration; the rate of excretion of the specific compound employed; the duration of the treatment; drugs used in combination or coincidental with the specific compound employed and like factors well known in the medical arts. For example, it is well within the skill of the art to start doses of a compound at levels lower than those required to achieve the desired therapeutic effect and to gradually increase the dosage until the desired effect is achieved. If desired, then the effective daily dose can be divided into multiple doses for purposes of administration. Consequently, single dose compositions can contain such amounts or submultiples thereof to make up the daily dose. The dosage can be adjusted by the individual physician in the event of any contraindications. Dosage can vary, and can be administered in one or more dose administrations daily, for one or several days. Guidance can be found in the literature for appropriate dosages for given classes of pharmaceutical products. In further various aspects, a preparation can be administered in a "prophylactically effective amount"; that is, an amount effective for prevention of a disease or condition.

As used herein, LoxaSperse™ refers to an excipient base powder comprising a blend of micronized xylitol and poloxamers. Such base compositions are known to those skilled in the art. LoxaSperse™ is manufactured by PCCA (Houston, Tex.) and is used as a chemical dispersing or solubilizing agent, thereby improving the solubility and dispersibility of poorly water soluble active pharmaceutical ingredients (APIs) or agents. LoxaSperse™ can be obtained from a bulk source.

As used herein, XyliFos™ refers to an excipient base powder comprising xylitol, poloxamer 407, hydroxylpropyl betadex, and epigallocatechin gallate. XyliFos™ is manufactured by PCCA (Houston, Tex.) and is used as a chemical dispersing or solubilizing agent, thereby improving the solubility and dispersibility of poorly water soluble active pharmaceutical ingredients (APIs) or agents. XyliFos™ can be obtained from a bulk source.

Anti-fungal agents are known to the art. The art generally recognizes several categories of anti-fungal agents including (1) azoles (imidazoles), (2) antimetabolites, (3) allylamines, (4) morpholine, (5) glucan synthesis inhibitors (echinocandins), (6) polyenes, (7) benoxaaborale; (8) other antifungal/onychomycosis agents, and (9) new classes of antifungal/onychomycosis agents.

Disclosed are the components to be used to prepare a composition of the invention as well as the compositions themselves to be used within the methods disclosed herein. These and other materials are disclosed herein, and it is understood that when combinations, subsets, interactions, groups, etc. of these materials are disclosed that while specific reference of each various individual and collective combinations and permutation of these compounds cannot be explicitly disclosed, each is specifically contemplated and described herein. For example, if a particular compound is disclosed and discussed and a number of modifications that can be made to a number of molecules including the compounds are discussed, specifically contemplated is each and every combination and permutation of the compound and the modifications that are possible unless specifically indicated to the contrary. Thus, if a class of molecules A, B, and C are disclosed as well as a class of molecules D, E, and F and an example of a combination molecule, A-D is disclosed, then even if each is not individually recited each is individually and collectively contemplated meaning combinations, A-E, A-F, B-D, B-E, B-F, C-D, C-E, and C-F are considered disclosed. Likewise, any subset or combination of these is also disclosed. Thus, for example, the sub-group of A-E, B-F, and C-E would be considered disclosed. This concept applies to all aspects of this application including, but not limited to, steps in methods of making and using the compositions of the invention. Thus, if there are a variety of additional steps that can be performed it is understood that each of these additional steps can be performed with any specific embodiment or combination of embodiments of the methods of the invention.

B. Compositions

1. Compounded Compositions

Disclosed herein is a compounded composition for treating or preventing a fungal infection using a foot bath, the compounded composition comprising fluconazole and an excipient base powder comprising a blend of micronized xylitol and poloxamers.

Disclosed herein is a compounded composition comprising an anti-infective agent and an excipient base powder comprising a blend of micronized xylitol and poloxamers. A disclosed compounded composition can comprise a dry powder formulation. In an aspect, a disclosed compounded composition can be encapsulated in a capsule or in one or more capsules.

In an aspect of a disclosed compounded composition, an anti-infective agent can comprise an anti-fungal agent, an anti-bacterial agent, or a combination thereof. In an aspect, an anti-infective agent can comprise a dry powder and can be obtained from a bulk source.

In an aspect of a disclosed compounded composition, an excipient base powder comprising a blend a micronized xylitol and poloxamers can be LoxaSperse™ excipient base powder. In an aspect, an excipient base powder comprising a blend a micronized xylitol and poloxamers can be XyliFos™ excipient base powder. In an aspect, XyliFos™ excipient base powder can comprise xylitol, poloxamer 407, hydroxylpropyl betadex, and epigallocatechin gallate. In an aspect, an excipient base powder can be obtained from a bulk source.

In an aspect of a disclosed compounded composition, an anti-fungal agent can comprise abafungin, albaconazole, amorolfin, amphotericin b, anidulafungin, bifonazole, butenafine, butoconazole, candicidin, caspofungin, ciclopirox, clotrimazole, econazole, fenticonazole, filipin, fluconazole, flucytosine, griseofulvin, haloprogin, hamycin, isavuconazole, isoconazole, itraconazole, ketoconazole, micafungin, miconazole, naftifine, natamycin, nystatin, omoconazole, oxiconazole, polygodial, posaconazole, ravuconazole, rimocidin, sertaconazole, sulconazole, terbinafine, terconazole, tioconazole, tolnaftate, undecylenic acid, voriconazole, or a combination thereof. In an aspect, an anti-fungal agent can comprise fluconazole, itraconazole, voriconazole, or a combination thereof. In an aspect, an anti-fungal agent can comprise fluconazole. In an aspect, an anti-fungal agent can comprise itraconazole or voriconazole or a combination thereof.

In an aspect, the ratio of an anti-fungal agent to excipient base powder in a disclosed compounded composition can be from about 1:60 to about 1:3. In an aspect, the ratio of an anti-fungal agent to excipient base powder in a disclosed compounded composition can be from about 1:60 to about 1:6. In an aspect, the ratio of an anti-fungal agent to excipient base powder in a disclosed compounded composition can be from about 1:30 to about 1:3. In an aspect, the ratio of an anti-fungal agent to excipient base powder in a disclosed compounded composition can be from about 1:20 to about 1:2. In an aspect, the ratio of an anti-fungal agent to excipient base powder in a disclosed compounded composition can be about 1:15. In an aspect, the amount of fluconazole in a disclosed compounded composition can be from about 200 mg to about 1000 mg and the amount of excipient base powder can be about 3 g. In an aspect, the amount of fluconazole in a disclosed compounded composition can be about 200 mg and the amount of excipient base powder can be about 3 g. In an aspect, the amount of fluconazole in a disclosed compounded composition can be about 1000 mg and the amount of excipient base powder can be about 3 g. In an aspect, the amount of itraconazole or voriconazole or a combination thereof in a disclosed compounded composition can be from about 50 mg to about 500 mg and the amount of excipient base powder can be about 3 g. In an aspect, the amount of itraconazole or voriconazole or a combination thereof in a disclosed compounded composition can be about 200 mg and the amount of excipient base powder can be about 3 g.

In an aspect of a disclosed compounded composition, an anti-bacterial agent can comprise afenide, amikacin, amoxicillin, ampicillin, arsphenamine, azithromycin, azlocillin, aztreonam, bacampicillin, bacitracin, carbacephem (loracarbef), carbenicillin, cefaclor, cefadroxil, cefalotin, cefamandole, cefazolin, cefdinir, cefditoren, cefepime, cefixime, cefoperazone, cefotaxime, cefoxitin, cefpodoxime, cefprozil, ceftazidime, ceftibuten, ceftizoxime, ceftobiprole, ceftriaxone, cefuroxime, cephalexin, chloramphenicol, chlorhexidine, ciprofloxacin, clarithromycin, clavulanic acid, clindamycin, cloxacillin, colimycin, colistimethate teicoplanin, colistin, demeclocycline, dicloxacillin, dirithromycin, doripenem, doxycycline, efprozil, enoxacin, ertapenem, erythromycin, ethambutol, flucloxacillin, fosfomycin, furazolidone, gatifloxacin, gemifloxacin, geldanamycin, gemifloxacin, gentamicin, grepafloxacin, herbimycin, imipenem, isoniazid, kanamycin, levofloxacin, lincomycin, linezolid, lomefloxacin, meropenem, meticillin, metronidazole, mezlocillin, minocycline, mitomycin, moxifloxacin, mupirocin, nafcillin, neomycin, netilmicin, nitrofurantoin, norfloxacin, ofloxacin, oxacillin, oxytetracycline, paromomycin, penicillin G, penicillin V, piperacillin, pivmecillinam, platensimycin, polymyxin B, prontosil, pvampicillin, pyrazinamide, quinupristin/dalfopristin, rifampicin, rifampin, roxithromycin, sparfloxacin, spectinomycin, spiramycin, sulbactam, sulfacetamide, sulfamethizole, sulfamethoxazole, sulfanilimide, sulfisoxazole, sulphonamides, sultamicillin, telithromycin, tetracycline, thiamphenicol, ticarcillin, tobramycin, trimethoprim, trimethoprim-sulfamethoxazole, troleandomycin, trovafloxacin, or a combination thereof. In an aspect, an anti-bacterial agent can comprise a quinolone. In an aspect, a quinolone can comprise ciprofloxacin, enoxacin, gatifloxacin, gemifloxacin, grepafloxacin, levofloxacin, lomefloxacin, moxifloxacin, nalidixic acid, norfloxacin, ofloxacin, sparfloxacin, trovafloxacin, or a combination thereof. In an aspect, a quinolone can comprise levofloxacin. In an aspect, an anti-bacterial agent can comprise an aminoglycoside. In an aspect, an aminoglycoside can comprise amikacin, gentamicin, kanamycin, neomycin, streptomycin, tobramycin, or a combination thereof. In an aspect, an aminoglycoside can comprise tobramycin.

In an aspect, a disclosed compounded composition can comprise one or more additional anti-infective agents. In an aspect, an additional anti-infective agent can comprise an anti-fungal agent, an anti-bacterial agent, or a combination thereof. In an aspect, an anti-infective agent can comprise a dry powder and can be obtained from a bulk source.

In an aspect, the ratio of an additional anti-infective agent to excipient base powder in a disclosed compounded composition can be from about 1:60 to about 1:3. In an aspect, the ratio of an additional anti-infective agent to excipient base powder in a disclosed compounded composition can be from about 1:60 to about 1:6. In an aspect, the ratio of an additional anti-infective agent to excipient base powder in a disclosed compounded composition can be from about 1:30 to about 1:3. In an aspect, the ratio of an additional anti-infective agent to excipient base powder can be from about 1:20 to about 1:2. In an aspect, the ratio of additional anti-infective agent to excipient base powder can be about 1:15.

In an aspect, a disclosed compounded composition can be used in a method to treat or prevent a fungal infection affecting the skin of at least a portion of a subject's foot or feet. In an aspect, a disclosed compounded composition can be used in a method to prevent a fungal infection affecting the nail of at least one toe on a subject's foot or feet.

Disclosed herein is a compounded composition comprising an anti-fungal agent and an excipient base powder comprising a blend of micronized xylitol and poloxamers. A compounded composition can comprise a dry powder formulation. In an aspect, a disclosed compounded composition can be encapsulated in a capsule or in one or more capsules. In an aspect, an anti-fungal agent can comprise a dry powder and can be obtained from a bulk source.

In an aspect of a disclosed compounded composition, an excipient base powder comprising a blend a micronized xylitol and poloxamers can be LoxaSperse™ excipient base powder. In an aspect, an excipient base powder comprising a blend a micronized xylitol and poloxamers can be XyliFos™ excipient base powder. In an aspect, XyliFos™ excipient base powder can comprise xylitol, poloxamer 407, hydroxylpropyl betadex, and epigallocatechin gallate. In an aspect, an excipient base powder can be obtained from a bulk source.

In an aspect of a disclosed compounded composition, an anti-fungal agent can comprise abafungin, albaconazole, amorolfin, amphotericin b, anidulafungin, bifonazole, butenafine, butoconazole, candicidin, caspofungin, ciclopirox, clotrimazole, econazole, fenticonazole, filipin, fluconazole, flucytosine, griseofulvin, haloprogin, hamycin, isavuconazole, isoconazole, itraconazole, ketoconazole, micafungin, miconazole, naftifine, natamycin, nystatin, omoconazole, oxiconazole, polygodial, posaconazole, ravuconazole, rimocidin, sertaconazole, sulconazole, terbinafine, terconazole, tioconazole, tolnaftate, undecylenic acid, voriconazole, or a combination thereof. In an aspect, an anti-fungal agent can comprise fluconazole, itraconazole, voriconazole, or a combination thereof. In an aspect, an anti-fungal agent can comprise fluconazole. In an aspect, an anti-fungal agent can comprise itraconazole or voriconazole or a combination thereof.

In an aspect, the ratio of an anti-fungal agent to excipient base powder in a disclosed compounded composition can be from about 1:60 to about 1:3. In an aspect, the ratio of an anti-fungal agent to excipient base powder in a disclosed compounded composition can be from about 1:60 to about 1:6. In an aspect, the ratio of an anti-fungal agent to excipient base powder in a disclosed compounded composition can be from about 1:30 to about 1:3. In an aspect, the ratio of an anti-fungal agent to excipient base powder in a disclosed compounded composition can be from about 1:20 to about 1:2. In an aspect, the amount of fluconazole in a disclosed compounded composition can be from about 200 mg to about 1000 mg and the amount of excipient base powder can be about 3 g. In an aspect, the amount of fluconazole in a disclosed compounded composition can be about 200 mg and the amount of excipient base powder can be about 3 g. In an aspect, the amount of fluconazole in a disclosed compounded composition can be about 1000 mg and the amount of excipient base powder can be about 3 g. In an aspect, the amount of itraconazole or voriconazole or a combination thereof in a disclosed compounded composition can be from about 50 mg to about 500 mg and the amount of excipient base powder can be about 3 g. In an aspect, the amount of itraconazole or voriconazole or a combination thereof in a disclosed compounded composition can be from about 200 mg and the amount of excipient base powder can be about 3 g.

In an aspect, a disclosed compounded composition can comprise one or more additional anti-infective agents. In an aspect, an additional anti-infective agent can comprise an anti-fungal agent, an anti-bacterial agent, or a combination thereof. In an aspect, an anti-infective agent can comprise a dry powder and can be obtained from a bulk source.

In an aspect of a disclosed compounded composition, an anti-bacterial agent can comprise afenide, amikacin, amoxicillin, ampicillin, arsphenamine, azithromycin, azlocillin, aztreonam, bacampicillin, bacitracin, carbacephem (loracarbef), carbenicillin, cefaclor, cefadroxil, cefalotin, cefamandole, cefazolin, cefdinir, cefditoren, cefepime, cefixime, cefoperazone, cefotaxime, cefoxitin, cefpodoxime, cefprozil, ceftazidime, ceftibuten, ceftizoxime, ceftobiprole, ceftriaxone, cefuroxime, cephalexin, chloramphenicol, chlorhexidine, ciprofloxacin, clarithromycin, clavulanic acid, clindamycin, cloxacillin, colimycin, colistimethate teicoplanin, colistin, demeclocycline, dicloxacillin, dirithromycin, doripenem, doxycycline, efprozil, enoxacin, ertapenem, erythromycin, ethambutol, flucloxacillin, fosfomycin, furazolidone, gatifloxacin, geldanamycin, gemifloxacin, gemifloxacin, gentamicin, grepafloxacin, herbimycin, imipenem, isoniazid, kanamycin, levofloxacin, lincomycin, linezolid, lomefloxacin, meropenem, meticillin, metronidazole, mezlocillin, minocycline, mitomycin, moxifloxacin, mupirocin, nafcillin, neomycin, netilmicin, nitrofurantoin, norfloxacin, ofloxacin, oxacillin, oxytetracycline, paromomycin, penicillin G, penicillin V, piperacillin, pivmecillinam, platensimycin, polymyxin B, prontosil, pvampicillin, pyrazinamide, quinupristin/dalfopristin, rifampicin, rifampin, roxithromycin, sparfloxacin, spectinomycin, spiramycin, sulbactam, sulfacetamide, sulfamethizole, sulfamethoxazole, sulfanilimide, sulfisoxazole, sulphonamides, sultamicillin, telithromycin, tetracycline, thiamphenicol, ticarcillin, tobramycin, trimethoprim, trimethoprim-sulfamethoxazole, troleandomycin, trovafloxacin, or a combination thereof. In an aspect, an anti-bacterial agent can comprise a quinolone. In an aspect, a quinolone can comprise ciprofloxacin, enoxacin, gatifloxacin, gemifloxacin, grepafloxacin, levofloxacin, lomefloxacin, moxifloxacin, nalidixic acid, norfloxacin, ofloxacin, sparfloxacin, trovafloxacin, or a combination thereof. In an aspect, a quinolone can comprise levofloxacin. In an aspect, an anti-bacterial agent can comprise an aminoglycoside. In an aspect, an aminoglycoside can comprise amikacin, gentamicin, kanamycin, neomycin, streptomycin, tobramycin, or a combination thereof. In an aspect, an aminoglycoside can comprise tobramycin.

In an aspect, the ratio of an additional anti-infective agent to excipient base powder in a disclosed compounded composition can be from about 1:60 to about 1:3. In an aspect, the ratio of an additional anti-infective agent to excipient base powder in a disclosed compounded composition can be from about 1:60 to about 1:6. In an aspect, the ratio of an additional anti-infective agent to excipient base powder in a disclosed compounded composition can be from about 1:30 to about 1:3. In an aspect, the ratio of an additional anti-infective agent to excipient base powder can be from about 1:20 to about 1:2. In an aspect, the ratio of additional anti-infective agent to excipient base powder can be about 1:15.

In an aspect, a disclosed compounded composition can be used in a method to treat or prevent a fungal infection affecting the skin of at least a portion of a subject's foot or feet. In an aspect, a disclosed compounded composition can be used in a method to prevent a fungal infection affecting the nail of at least one toe on a subject's foot or feet.

In an aspect, a disclosed compounded composition can comprise one or more excipients or additives. In an aspect, excipients or additives include, but are not limited to, the following: solvents, surfactants, humectants, preservatives, flavorings, stabilizers (including antioxidants), binders, and colorants.

Disclosed herein is a compounded composition, comprising fluconazole and an excipient base powder comprising a blend of micronized xylitol and poloxamers. In an aspect, a disclosed compounded composition can be a dry powder formulation. In an aspect, a disclosed compounded composition can be encapsulated in a capsule or in one or more capsules. In an aspect, fluconazole can comprise a dry powder and can be obtained from a bulk source.

In an aspect of a disclosed compounded composition, an excipient base powder comprising a blend a micronized xylitol and poloxamers can be LoxaSperse™ excipient base powder. In an aspect, an excipient base powder comprising a blend a micronized xylitol and poloxamers can be XyliFos™ excipient base powder. In an aspect, XyliFos™ excipient base powder can comprise xylitol, poloxamer 407, hydroxylpropyl betadex, and epigallocatechin gallate. In an aspect, an excipient base powder can be obtained from a bulk source.

In an aspect, the ratio of fluconazole to excipient base powder in a disclosed compounded composition can be from about 1:60 to about 1:3. In an aspect, the ratio of fluconazole to excipient base powder in a disclosed compounded composition can be from about 1:60 to about 1:6. In an aspect, the ratio of fluconazole to excipient base powder in a disclosed compounded composition can be from about 1:30 to about 1:3. In an aspect, the ratio of fluconazole to excipient base powder in a disclosed compounded composition can be from about 1:20 to about 1:2. In an aspect, the ratio of fluconazole to excipient base powder in a disclosed compounded composition can be about 1:15.

In an aspect, the amount of fluconazole in a disclosed compounded composition can be from about 200 mg to about 1000 mg and the amount of excipient base powder can be about 3 g. In an aspect, the amount of fluconazole in a disclosed compounded composition can be about 200 mg and the amount of excipient base powder can be about 3 g. In an aspect, the amount of fluconazole in a disclosed compounded composition can be about 1000 mg and the amount of excipient base powder can be about 3 g.

In an aspect, a disclosed compounded composition can comprise one or more additional anti-infective agents. In an aspect, an additional anti-infective agent can comprise an anti-fungal agent, an anti-bacterial agent, or a combination thereof. In an aspect, an anti-infective agent can comprise a dry powder and can be obtained from a bulk source. In an aspect, the ratio of an additional anti-infective agent to excipient base powder in a disclosed compounded composition can be from about 1:60 to about 1:3. In an aspect, the ratio of an additional anti-infective agent to excipient base powder in a disclosed compounded composition can be from about 1:60 to about 1:6. In an aspect, the ratio of an additional anti-infective agent to excipient base powder in a disclosed compounded composition can be from about 1:30 to about 1:3. In an aspect, the ratio of an additional anti-infective agent to excipient base powder can be from about 1:20 to about 1:2. In an aspect, the ratio of additional anti-infective agent to excipient base powder can be about 1:15.

In an aspect of a disclosed compounded composition, an anti-fungal agent can comprise abafungin, albaconazole, amorolfin, amphotericin b, anidulafungin, bifonazole, butenafine, butoconazole, candicidin, caspofungin, ciclopirox, clotrimazole, econazole, fenticonazole, filipin, fluconazole, flucytosine, griseofulvin, haloprogin, hamycin, isavuconazole, isoconazole, itraconazole, ketoconazole, micafungin, miconazole, naftifine, natamycin, nystatin, omoconazole, oxiconazole, polygodial, posaconazole, ravuconazole, rimocidin, sertaconazole, sulconazole, terbinafine, terconazole, tioconazole, tolnaftate, undecylenic acid, voriconazole, or a combination thereof. In an aspect, an anti-fungal agent can comprise fluconazole, itraconazole, voriconazole, or a combination thereof. In an aspect, an anti-fungal agent can comprise fluconazole. In an aspect, an anti-fungal agent can comprise itraconazole or voriconazole or a combination thereof.

In an aspect of a disclosed compounded composition, an anti-bacterial agent of a disclosed compounded composition can comprise afenide, amikacin, amoxicillin, ampicillin, arsphenamine, azithromycin, azlocillin, aztreonam, bacampicillin, bacitracin, carbacephem (loracarbef), carbenicillin, cefaclor, cefadroxil, cefalotin, cefamandole, cefazolin, cefdinir, cefditoren, cefepime, cefixime, cefoperazone, cefotaxime, cefoxitin, cefpodoxime, cefprozil, ceftazidime, ceftibuten, ceftizoxime, ceftobiprole, ceftriaxone, cefuroxime, cephalexin, chloramphenicol, chlorhexidine, ciprofloxacin, clarithromycin, clavulanic acid, clindamycin, cloxacillin, colimycin, colistimethate teicoplanin, colistin, demeclocycline, dicloxacillin, dirithromycin, doripenem, doxycycline, efprozil, enoxacin, ertapenem, erythromycin, ethambutol, flucloxacillin, fosfomycin, furazolidone, gatifloxacin, geldanamycin, gemifloxacin, gentamicin, grepafloxacin, herbimycin, imipenem, isoniazid, kanamycin, levofloxacin, lincomycin, linezolid, lomefloxacin, meropenem, meticillin, metronidazole, mezlocillin, minocycline, mitomycin, moxifloxacin, mupirocin, nafcillin, neomycin, netilmicin, nitrofurantoin, norfloxacin, ofloxacin, oxacillin, oxytetracycline, paromomycin, penicillin G, penicillin V, piperacillin, pivmecillinam, platensimycin, polymyxin B, prontosil, pvampicillin, pyrazinamide, quinupristin/dalfopristin, rifampicin, rifampin, roxithromycin, sparfloxacin, spectinomycin, spiramycin, sulbactam, sulfacetamide, sulfamethizole, sulfamethoxazole, sulfanilimide, sulfisoxazole, sulphonamides, sultamicillin, telithromycin, tetracycline, thiamphenicol, ticarcillin, tobramycin, trimethoprim, trimethoprim-sulfamethoxazole, troleandomycin, trovafloxacin, or a combination thereof. In an aspect, an anti-bacterial agent can comprise a quinolone. In an aspect, a quinolone can comprise ciprofloxacin, enoxacin, gatifloxacin, gemifloxacin, grepafloxacin, levofloxacin, lomefloxacin, moxifloxacin, nalidixic acid, norfloxacin, ofloxacin, sparfloxacin, trovafloxacin, or a combination thereof. In an aspect, a quinolone can comprise levofloxacin. In an aspect, an anti-bacterial agent can comprise an aminoglycoside. In an aspect, an aminoglycoside can comprise amikacin, gentamicin, kanamycin, neomycin, streptomycin, tobramycin, or a combination thereof. In an aspect, an aminoglycoside can comprise tobramycin.

Disclosed herein is a compounded composition, comprising itraconazole, voriconazole, or a combination thereof, and an excipient base powder comprising a blend of micronized xylitol and poloxamers. A disclosed compounded composition can comprise a dry powder formulation. In an aspect, a disclosed compounded composition can be encapsulated in a capsule or in one or more capsules. In an aspect, itraconazole, voriconazole, or both can comprise a dry powder and can be obtained from a bulk source.

In an aspect of a disclosed compounded composition, an excipient base powder comprising a blend a micronized xylitol and poloxamers can be LoxaSperse™ excipient base powder. In an aspect, an excipient base powder comprising a blend a micronized xylitol and poloxamers can be XyliFos™ excipient base powder. In an aspect, XyliFos™ excipient base powder can comprise xylitol, poloxamer 407, hydroxylpropyl betadex, and epigallocatechin gallate. In an aspect, an excipient base powder can be obtained from a bulk source.

In an aspect, the ratio of itraconazole, voriconazole, or a combination thereof to excipient base powder in a disclosed compounded composition can be from about 1:60 to about 1:3. In an aspect, the ratio of itraconazole, voriconazole, or a combination thereof to excipient base powder in a disclosed compounded composition can be from about 1:60 to about 1:6. In an aspect, the ratio of itraconazole, voriconazole, or a combination thereof to excipient base powder in a disclosed compounded can be from about 1:30 to about 1:3. In an aspect, the ratio of itraconazole, voriconazole, or a combination thereof to excipient base powder in a disclosed compounded composition can be from about 1:20 to about 1:2. In an aspect, the ratio of itraconazole, voriconazole, or a combination thereof to excipient base powder in a disclosed compounded composition can be about 1:15.

In an aspect, the amount of itraconazole, voriconazole, or a combination thereof in a disclosed compounded composition can be from about 50 mg to about 1000 mg and the amount of excipient base powder can be about 3 g. In an aspect, the amount of itraconazole, voriconazole, or a combination thereof in a disclosed compounded composition can be from about 200 mg to about 500 mg and the amount of excipient base powder can be about 3 g. In an aspect, the amount of itraconazole, voriconazole, or a combination thereof in a disclosed compounded composition can be about 50 mg and the amount of excipient base powder can be about 3 g. In an aspect, the amount of itraconazole, voriconazole, or a combination thereof in a disclosed compounded composition can be about 500 mg and the amount of excipient base powder can be about 3 g.

In an aspect, a disclosed compounded composition can comprise one or more additional anti-infective agents. In an aspect, an additional anti-infective agent can comprise an anti-fungal agent, an anti-bacterial agent, or a combination thereof. In an aspect, an anti-infective agent can comprise a dry powder and can be obtained from a bulk source. In an aspect, the ratio of an additional anti-infective agent to excipient base powder in a disclosed compounded composition can be from about 1:60 to about 1:3. In an aspect, the ratio of an additional anti-infective agent to excipient base powder in a disclosed compounded composition can be from about 1:60 to about 1:6. In an aspect, the ratio of an additional anti-infective agent to excipient base powder in a disclosed compounded composition can be from about 1:30 to about 1:3. In an aspect, the ratio of an additional anti-infective agent to excipient base powder can be from about 1:20 to about 1:2. In an aspect, the ratio of additional anti-infective agent to excipient base powder can be about 1:15.

In an aspect of a disclosed compounded composition, an anti-fungal agent can comprise abafungin, albaconazole, amorolfin, amphotericin b, anidulafungin, bifonazole, butenafine, butoconazole, candicidin, caspofungin, ciclopirox, clotrimazole, econazole, fenticonazole, filipin, fluconazole, flucytosine, griseofulvin, haloprogin, hamycin, isavuconazole, isoconazole, itraconazole, ketoconazole, micafungin, miconazole, naftifine, natamycin, nystatin, omoconazole, oxiconazole, polygodial, posaconazole, ravuconazole, rimocidin, sertaconazole, sulconazole, terbinafine, terconazole, tioconazole, tolnaftate, undecylenic acid, voriconazole, or a combination thereof. In an aspect, an anti-fungal agent can comprise fluconazole, itraconazole, voriconazole, or a combination thereof. In an aspect, an anti-fungal agent can comprise fluconazole. In an aspect, an anti-fungal agent can comprise itraconazole or voriconazole or a combination thereof.

In an aspect of a disclosed compounded composition, an anti-bacterial agent can comprise afenide, amikacin, amoxicillin, ampicillin, arsphenamine, azithromycin, azlocillin, aztreonam, bacampicillin, bacitracin, carbacephem (loracarbef), carbenicillin, cefaclor, cefadroxil, cefalotin, cefamandole, cefazolin, cefdinir, cefditoren, cefepime, cefixime, cefoperazone, cefotaxime, cefoxitin, cefpodoxime, cefprozil, ceftazidime, ceftibuten, ceftizoxime, ceftobiprole, ceftriaxone, cefuroxime, cephalexin, chloramphenicol, chlorhexidine, ciprofloxacin, clarithromycin, clavulanic acid, clindamycin, cloxacillin, colimycin, colistimethate teicoplanin, colistin, demeclocycline, dicloxacillin, dirithromycin, doripenem, doxycycline, efprozil, enoxacin, ertapenem, erythromycin, ethambutol, flucloxacillin, fosfomycin, furazolidone, gatifloxacin, geldanamycin, gemifloxacin, gentamicin, grepafloxacin, herbimycin, imipenem, isoniazid, kanamycin, levofloxacin, lincomycin, linezolid, lomefloxacin, meropenem, meticillin, metronidazole, mezlocillin, minocycline, mitomycin, moxifloxacin, mupirocin, nafcillin, neomycin, netilmicin, nitrofurantoin, norfloxacin, ofloxacin, oxacillin, oxytetracycline, paromomycin, penicillin G, penicillin V, piperacillin, pivmecillinam, platensimycin, polymyxin B, prontosil, pvampicillin, pyrazinamide, quinupristin/dalfopristin, rifampicin, rifampin, roxithromycin, sparfloxacin, spectinomycin, spiramycin, sulbactam, sulfacetamide, sulfamethizole, sulfamethoxazole, sulfanilimide, sulfisoxazole, sulphonamides, sultamicillin, telithromycin, tetracycline, thiamphenicol, ticarcillin, tobramycin, trimethoprim, trimethoprim-sulfamethoxazole, troleandomycin, trovafloxacin, or a combination thereof. In an aspect, an anti-bacterial agent can comprise a quinolone. In an aspect, a quinolone can comprise ciprofloxacin, enoxacin, gatifloxacin, gemifloxacin, grepafloxacin, levofloxacin, lomefloxacin, moxifloxacin, nalidixic acid, norfloxacin, ofloxacin, sparfloxacin, trovafloxacin, or a combination thereof. In an aspect, a quinolone can comprise levofloxacin. In an aspect, an anti-bacterial agent can comprise an aminoglycoside. In an aspect, an aminoglycoside can comprise amikacin, gentamicin, kanamycin, neomycin, streptomycin, tobramycin, or a combination thereof. In an aspect, an aminoglycoside can comprise tobramycin.

In an aspect, a disclosed compounded composition can be used in a method to treat or prevent a fungal infection affecting the skin of at least a portion of a subject's foot or feet. In an aspect, a disclosed compounded composition can be used in a method to prevent a fungal infection affecting the nail of at least one toe on a subject's foot or feet.

In an aspect, a disclosed compounded composition can comprise one or more excipients or additives. In an aspect, excipients or additives include, but are not limited to, the following: solvents, surfactants, humectants, preservatives, flavorings, stabilizers (including antioxidants), binders, and colorants.

Disclosed herein is a compounded composition comprising an anti-fungal agent, an excipient base powder comprising a blend of micronized xylitol and poloxamers, and one or more additional anti-infective agents. A disclosed compounded composition can comprise a dry powder formulation. In an aspect, a disclosed compounded composition can be encapsulated in a capsule or in one or more capsules. In an aspect, an anti-fungal agent can comprise a dry powder and can be obtained from a bulk source.

In an aspect of a disclosed compounded composition, an anti-infective agent can comprise an anti-fungal agent, an anti-bacterial agent, or a combination thereof. In an aspect, an anti-infective agent can comprise a dry powder and can be obtained from a bulk source.

In an aspect of a disclosed compounded composition, an excipient base powder comprising a blend a micronized xylitol and poloxamers can be LoxaSperse™ excipient base powder. In an aspect, an excipient base powder comprising a blend a micronized xylitol and poloxamers can be XyliFos™ excipient base powder. In an aspect, XyliFos™ excipient base powder can comprise xylitol, poloxamer 407, hydroxylpropyl betadex, and epigallocatechin gallate. In an aspect, an excipient base powder can be obtained from a bulk source.

In an aspect, the ratio of an additional anti-infective agent to excipient base powder in a disclosed compounded composition can be from about 1:60 to about 1:3. In an aspect, the ratio of an additional anti-infective agent to excipient base powder in a disclosed compounded composition can be from about 1:60 to about 1:6. In an aspect, the ratio of an additional anti-infective agent to excipient base powder in a disclosed compounded composition can be from about 1:30 to about 1:3. In an aspect, the ratio of an additional anti-infective agent to excipient base powder can be from about 1:20 to about 1:2. In an aspect, the ratio of additional anti-infective agent to excipient base powder can be about 1:15.

In an aspect of a disclosed compounded composition, an anti-fungal agent can comprise abafungin, albaconazole, amorolfin, amphotericin b, anidulafungin, bifonazole, butenafine, butoconazole, candicidin, caspofungin, ciclopirox, clotrimazole, econazole, fenticonazole, filipin, fluconazole, flucytosine, griseofulvin, haloprogin, hamycin, isavuconazole, isoconazole, itraconazole, ketoconazole, micafungin, miconazole, naftifine, natamycin, nystatin, omoconazole, oxiconazole, polygodial, posaconazole, ravuconazole, rimocidin, sertaconazole, sulconazole, terbinafine, terconazole, tioconazole, tolnaftate, undecylenic acid, voriconazole, or a combination thereof. In an aspect, an anti-fungal agent can comprise fluconazole, itraconazole, voriconazole, or a combination thereof. In an aspect, an anti-fungal agent can comprise fluconazole. In an aspect, an anti-fungal agent can comprise itraconazole or voriconazole or a combination thereof.

In an aspect, the ratio of an anti-fungal agent to excipient base powder in a disclosed compounded composition can be from about 1:60 to about 1:3. In an aspect, the ratio of an anti-fungal agent to excipient base powder in a disclosed compounded composition can be from about 1:60 to about 1:6. In an aspect, the ratio of an anti-fungal agent to excipient base powder in a disclosed compounded composition can be from about 1:30 to about 1:3. In an aspect, the ratio of an anti-fungal agent to excipient base powder in a disclosed compounded composition can be from about 1:20 to about 1:2. In an aspect, the ratio of an anti-fungal agent to excipient base powder in a disclosed compounded composition can be about 1:15. In an aspect, the amount of fluconazole in a disclosed compounded composition can be from about 200 mg to about 1000 mg and the amount of excipient base powder can be about 3 g. In an aspect, the amount of fluconazole in a disclosed compounded composition can be about 200 mg and the amount of excipient base powder can be about 3 g. In an aspect, the amount of fluconazole in a disclosed compounded composition can be about 1000 mg and the amount of excipient base powder can be about 3 g. In an aspect, the amount of itraconazole or voriconazole or a combination thereof in a disclosed compounded composition can be from about 50 mg to about 500 mg and the amount of excipient base powder can be about 3 g. In an aspect, the amount of itraconazole or voriconazole or a combination thereof in a disclosed compounded composition can be from about 200 mg and the amount of excipient base powder can be about 3 g.

In an aspect of a disclosed compounded composition, an anti-bacterial agent can comprise afenide, amikacin, amoxicillin, ampicillin, arsphenamine, azithromycin, azlocillin, aztreonam, bacampicillin, bacitracin, carbacephem (loracarbef), carbenicillin, cefaclor, cefadroxil, cefalotin, cefamandole, cefazolin, cefdinir, cefditoren, cefepime, cefixime, cefoperazone, cefotaxime, cefoxitin, cefpodoxime, cefprozil, ceftazidime, ceftibuten, ceftizoxime, ceftobiprole, ceftriaxone, cefuroxime, cephalexin, chloramphenicol, chlorhexidine, ciprofloxacin, clarithromycin, clavulanic acid, clindamycin, cloxacillin, colimycin, colistimethate teicoplanin, colistin, demeclocycline, dicloxacillin, dirithromycin, doripenem, doxycycline, efprozil, enoxacin, ertapenem, erythromycin, ethambutol, flucloxacillin, fosfomycin, furazolidone, gatifloxacin, geldanamycin, gemifloxacin, gentamicin, grepafloxacin, herbimycin, imipenem, isoniazid, kanamycin, levofloxacin, lincomycin, linezolid, lomefloxacin, meropenem, meticillin, metronidazole, mezlocillin, minocycline, mitomycin, moxifloxacin, mupirocin, nafcillin, neomycin, netilmicin, nitrofurantoin, norfloxacin, ofloxacin, oxacillin, oxytetracycline, paromomycin, penicillin G, penicillin V, piperacillin, pivmecillinam, platensimycin, polymyxin B, prontosil, pvampicillin, pyrazinamide, quinupristin/dalfopristin, rifampicin, rifampin, roxithromycin, sparfloxacin, spectinomycin, spiramycin, sulbactam, sulfacetamide, sulfamethizole, sulfamethoxazole, sulfanilimide, sulfisoxazole, sulphonamides, sultamicillin, telithromycin, tetracycline, thiamphenicol, ticarcillin, tobramycin, trimethoprim, trimethoprim-sulfamethoxazole, troleandomycin, trovafloxacin, or a combination thereof. In an aspect, an anti-bacterial agent can comprise a quinolone. In an aspect, a quinolone can comprise ciprofloxacin, enoxacin, gatifloxacin, gemifloxacin, grepafloxacin, levofloxacin, lomefloxacin, moxifloxacin, nalidixic acid, norfloxacin, ofloxacin, sparfloxacin, trovafloxacin, or a combination thereof. In an aspect, a quinolone can comprise levofloxacin. In an aspect, an anti-bacterial agent can comprise an aminoglycoside. In an aspect, an aminoglycoside can comprise amikacin, gentamicin, kanamycin, neomycin, streptomycin, tobramycin, or a combination thereof. In an aspect, an aminoglycoside can comprise tobramycin.

In an aspect, a disclosed compounded composition can be used in a method to treat or prevent a fungal infection affecting the skin of at least a portion of a subject's foot or feet. In an aspect, a disclosed compounded composition can be used in a method to prevent a fungal infection affecting the nail of at least one toe on a subject's foot or feet.

In an aspect, a disclosed compounded composition can comprise one or more excipients or additives. In an aspect, excipients or additives include, but are not limited to, the following: solvents, surfactants, humectants, preservatives, flavorings, stabilizers (including antioxidants), binders, and colorants.

2. Containers

Disclosed herein is a container comprising a disclosed compounded composition.

Disclosed herein is a container comprising a compounded composition, wherein the compounded composition comprises an anti-fungal agent and an excipient base powder comprising a blend of micronized xylitol and poloxamers. A disclosed compounded composition can comprise a dry powder formulation. In an aspect, a disclosed compounded composition can be encapsulated in a capsule or in one or more capsules. In an aspect, an anti-fungal agent can comprise a dry powder and can be obtained from a bulk source.

In an aspect of a disclosed container, an excipient base powder comprising a blend a micronized xylitol and poloxamers can be LoxaSperse™ excipient base powder. In an aspect, an excipient base powder comprising a blend a micronized xylitol and poloxamers can be XyliFos™ excipient base powder. In an aspect, XyliFos™ excipient base powder can comprise xylitol, poloxamer 407, hydroxypropyl betadex, and epigallocatechin gallate. In an aspect, an excipient base powder can be obtained from a bulk source.

In an aspect of a disclosed container, an anti-fungal agent can comprise abafungin, albaconazole, amorolfin, amphotericin b, anidulafungin, bifonazole, butenafine, butoconazole, candicidin, caspofungin, ciclopirox, clotrimazole, econazole, fenticonazole, filipin, fluconazole, flucytosine, griseofulvin, haloprogin, hamycin, isavuconazole, isoconazole, itraconazole, ketoconazole, micafungin, miconazole, naftifine, natamycin, nystatin, omoconazole, oxiconazole, polygodial, posaconazole, ravuconazole, rimocidin, sertaconazole, sulconazole, terbinafine, terconazole, tioconazole, tolnaftate, undecylenic acid, voriconazole, or a combination thereof. In an aspect, an anti-fungal agent can comprise fluconazole, itraconazole, voriconazole, or a combination thereof. In an aspect, an anti-fungal agent can comprise fluconazole. In an aspect, an anti-fungal agent can comprise itraconazole or voriconazole or a combination thereof.

In an aspect, the ratio of an anti-fungal agent to excipient base powder in a disclosed compounded composition can be from about 1:60 to about 1:3. In an aspect, the ratio of an anti-fungal agent to excipient base powder in a disclosed compounded composition can be from about 1:60 to about 1:6. In an aspect, the ratio of an anti-fungal agent to excipient base powder in a disclosed compounded composition can be from about 1:30 to about 1:3. In an aspect, the ratio of an anti-fungal agent to excipient base powder in a disclosed compounded composition can be from about 1:20 to about 1:2. In an aspect, the ratio of an anti-fungal agent to excipient base powder in a disclosed compounded composition can be about 1:15. In an aspect, the amount of fluconazole in a disclosed compounded composition can be from about 200 mg to about 1000 mg and the amount of excipient base powder can be about 3 g. In an aspect, the amount of fluconazole in a disclosed compounded composition can be about 200 mg and the amount of excipient base powder can be about 3 g. In an aspect, the amount of fluconazole in a disclosed compounded composition can be about 1000 mg and the amount of excipient base powder can be about 3 g. In an aspect, the amount of itraconazole or voriconazole or a combination thereof in a disclosed compounded composition can be from about 50 mg to about 500 mg and the amount of excipient base powder can be about 3 g. In an aspect, the amount of itraconazole or voriconazole or a combination thereof in a disclosed compounded composition can be from about 200 mg and the amount of excipient base powder can be about 3 g.

In an aspect of a disclosed container, a compounded composition can comprise one or more additional anti-infective agents. In an aspect, an additional anti-infective agent can comprise an anti-fungal agent, an anti-bacterial agent, or a combination thereof. In an aspect, an anti-infective agent can comprise a dry powder and can be obtained from a bulk source. In an aspect, the ratio of an additional anti-infective agent to excipient base powder in a disclosed compounded composition can be from about 1:60 to about 1:3. In an aspect, the ratio of an additional anti-infective agent to excipient base powder in a disclosed compounded composition can be from about 1:60 to about 1:6. In an aspect, the ratio of an additional anti-infective agent to excipient base powder in a disclosed compounded composition can be from about 1:30 to about 1:3. In an aspect, the ratio of an additional anti-infective agent to excipient base powder can be from about 1:20 to about 1:2. In an aspect, the ratio of additional anti-infective agent to excipient base powder can be about 1:15.

In an aspect of a disclosed container, an anti-bacterial agent can comprise afenide, amikacin, amoxicillin, ampicillin, arsphenamine, azithromycin, azlocillin, aztreonam, bacampicillin, bacitracin, carbacephem (loracarbef), carbenicillin, cefaclor, cefadroxil, cefalotin, cefamandole, cefazolin, cefdinir, cefditoren, cefepime, cefixime, cefoperazone, cefotaxime, cefoxitin, cefpodoxime, cefprozil, ceftazidime, ceftibuten, ceftizoxime, ceftobiprole, ceftriaxone, cefuroxime, cephalexin, chloramphenicol, chlorhexidine, ciprofloxacin, clarithromycin, clavulanic acid, clindamycin, cloxacillin, colimycin, colistimethate teicoplanin, colistin, demeclocycline, dicloxacillin, dirithromycin, doripenem, doxycycline, efprozil, enoxacin, ertapenem, erythromycin, ethambutol, flucloxacillin, fosfomycin, furazolidone, gatifloxacin, geldanamycin, gemifloxacin, gentamicin, grepafloxacin, herbimycin, imipenem, isoniazid, kanamycin, levofloxacin, lincomycin, linezolid, lomefloxacin, meropenem, meticillin, metronidazole, mezlocillin, minocycline, mitomycin, moxifloxacin, mupirocin, nafcillin, neomycin, netilmicin, nitrofurantoin, norfloxacin, ofloxacin, oxacillin, oxytetracycline, paromomycin, penicillin G, penicillin V, piperacillin, pivmecillinam, platensimycin, polymyxin B, prontosil, pvampicillin, pyrazinamide, quinupristin/dalfopristin, rifampicin, rifampin, roxithromycin, sparfloxacin, spectinomycin, spiramycin, sulbactam, sulfacetamide, sulfamethizole, sulfamethoxazole, sulfanilimide, sulfisoxazole, sulphonamides, sultamicillin, telithromycin, tetracycline, thiamphenicol, ticarcillin, tobramycin, trimethoprim, trimethoprim-sulfamethoxazole, troleandomycin, trovafloxacin, or a combination thereof. In an aspect, an anti-bacterial agent can comprise a quinolone. In an aspect, a quinolone can comprise ciprofloxacin, enoxacin, gatifloxacin, gemifloxacin, grepafloxacin, levofloxacin, lomefloxacin, moxifloxacin, nalidixic acid, norfloxacin, ofloxacin, sparfloxacin, trovafloxacin, or a combination thereof. In an aspect, a quinolone can comprise levofloxacin. In an aspect, an anti-bacterial agent can comprise an aminoglycoside. In an aspect, an aminoglycoside can comprise amikacin, gentamicin, kanamycin, neomycin, streptomycin, tobramycin, or a combination thereof. In an aspect, an aminoglycoside can comprise tobramycin.

In an aspect, a disclosed container can be a glass container and can comprise a stopper or a seal. In an aspect, a container can be a non-glass container and can comprise a stopper or a seal. In an aspect, a stopper can comprise siliconized or non-siliconized rubber. In an aspect, rubber can be bromobutyl rubber or chlorobutyl rubber. In an aspect, a stopper or seal can comprise metal. In an aspect, a stopper or seal can comprise a Teflon coating or a Teflon treatment. In an aspect, a container can be a disposable packet. In an aspect, a disposable packet can be moisture-free. In an aspect, a container can be a glass or non-glass vial. In an aspect, a vial can be a 25 mL vial, a 50 mL vial, a 75 mL via, a 100 mL vial, a 125 mL vial, a 150 mL vial, a 175 mL vial, a 200 mL vial, a 250 mL vial, a 300 mL vial, a 350 mL vial, a 400 mL vial, a 450 mL vial, a 500 mL vial, or a 1000 mL vial. In an aspect, a vial can be range in size from about 25 mL to about 1000 mL. In an aspect, a vial can comprise a capsule or one or more capsules, each encapsulating a disclosed compounded composition.

Disclosed herein is a container comprising a compounded composition, wherein the compounded composition comprises comprising an anti-fungal agent, an excipient base powder comprising a blend of micronized xylitol and poloxamers, and one or more additional anti-infective agents. In an aspect, a compounded composition can be a dry powder formulation. In an aspect, an anti-fungal agent can comprise a dry powder and can be obtained from a bulk source. In an aspect, a disclosed compounded composition can be encapsulated in a capsule or in one or more capsules.

In an aspect of a disclosed container, an excipient base powder comprising a blend a micronized xylitol and poloxamers can be LoxaSperse™ excipient base powder. In an aspect, an excipient base powder comprising a blend a micronized xylitol and poloxamers can be XyliFos™ excipient base powder. In an aspect, XyliFos™ excipient base powder can comprise xylitol, poloxamer 407, hydroxylpropyl betadex, and epigallocatechin gallate. In an aspect, an excipient base powder can be obtained from a bulk source.

In an aspect of a disclosed container, an anti-fungal agent can comprise abafungin, albaconazole, amorolfin, amphotericin b, anidulafungin, bifonazole, butenafine, butoconazole, candicidin, caspofungin, ciclopirox, clotrimazole, econazole, fenticonazole, filipin, fluconazole, flucytosine, griseofulvin, haloprogin, hamycin, isavuconazole, isoconazole, itraconazole, ketoconazole, micafungin, miconazole, naftifine, natamycin, nystatin, omoconazole, oxiconazole, polygodial, posaconazole, ravuconazole, rimocidin, sertaconazole, sulconazole, terbinafine, terconazole, tioconazole, tolnaftate, undecylenic acid, voriconazole, or a combination thereof. In an aspect, an anti-fungal agent can comprise fluconazole, itraconazole, voriconazole, or a combination thereof. In an aspect, an anti-fungal agent can comprise fluconazole. In an aspect, an anti-fungal agent can comprise itraconazole or voriconazole or a combination thereof.

In an aspect, the ratio of an anti-fungal agent to excipient base powder in a disclosed compounded composition can be from about 1:60 to about 1:3. In an aspect, the ratio of an anti-fungal agent to excipient base powder in a disclosed compounded composition can be from about 1:60 to about 1:6. In an aspect, the ratio of an anti-fungal agent to excipient base powder in a disclosed compounded composition can be from about 1:30 to about 1:3. In an aspect, the ratio of an anti-fungal agent to excipient base powder in a disclosed compounded composition can be from about 1:20 to about 1:2. In an aspect, the ratio of an anti-fungal agent to excipient base powder in a disclosed compounded composition can be about 1:15. In an aspect, the amount of fluconazole in a disclosed compounded composition can be from about 200 mg to about 1000 mg and the amount of excipient base powder can be about 3 g. In an aspect, the amount of fluconazole in a disclosed compounded composition can be about 200 mg and the amount of excipient base powder can be about 3 g. In an aspect, the amount of fluconazole in a disclosed compounded composition can be about 1000 mg and the amount of excipient base powder can be about 3 g. In an aspect, the amount of itraconazole or voriconazole or a combination thereof in a disclosed compounded composition can be from about 50 mg to about 500 mg and the amount of excipient base powder can be about 3 g. In an aspect, the amount of itraconazole or voriconazole or a combination thereof in a disclosed compounded composition can be from about 200 mg and the amount of excipient base powder can be about 3 g.

In an aspect of a disclosed container, an additional anti-infective agent can comprise an anti-fungal agent, an anti-bacterial agent, or a combination thereof. In an aspect, an anti-infective agent can comprise a dry powder and can be obtained from a bulk source. In an aspect, the ratio of an additional anti-infective agent to excipient base powder in a disclosed compounded composition can be from about 1:60 to about 1:3. In an aspect, the ratio of an additional anti-infective agent to excipient base powder in a disclosed compounded composition can be from about 1:60 to about 1:6. In an aspect, the ratio of an additional anti-infective agent to excipient base powder in a disclosed compounded composition can be from about 1:30 to about 1:3. In an aspect, the ratio of an additional anti-infective agent to excipient base powder can be from about 1:20 to about 1:2. In an aspect, the ratio of additional anti-infective agent to excipient base powder can be about 1:15.

In an aspect of a disclosed container, an anti-bacterial agent can comprise afenide, amikacin, amoxicillin, ampicillin, arsphenamine, azithromycin, azlocillin, aztreonam, bacampicillin, bacitracin, carbacephem (loracarbef), carbenicillin, cefaclor, cefadroxil, cefalotin, cefamandole, cefazolin, cefdinir, cefditoren, cefepime, cefixime, cefoperazone, cefotaxime, cefoxitin, cefpodoxime, cefprozil, ceftazidime, ceftibuten, ceftizoxime, ceftobiprole, ceftriaxone, cefuroxime, cephalexin, chloramphenicol, chlorhexidine, ciprofloxacin, clarithromycin, clavulanic acid, clindamycin, cloxacillin, colimycin, colistimethate teicoplanin, colistin, demeclocycline, dicloxacillin, dirithromycin, doripenem, doxycycline, efprozil, enoxacin, ertapenem, erythromycin, ethambutol, flucloxacillin, fosfomycin, furazolidone, gatifloxacin, geldanamycin, gemifloxacin, gentamicin, grepafloxacin, herbimycin, imipenem, isoniazid, kanamycin, levofloxacin, lincomycin, linezolid, lomefloxacin, meropenem, meticillin, metronidazole, mezlocillin, minocycline, mitomycin, moxifloxacin, mupirocin, nafcillin, neomycin, netilmicin, nitrofurantoin, norfloxacin, ofloxacin, oxacillin, oxytetracycline, paromomycin, penicillin G, penicillin V, piperacillin, pivmecillinam, platensimycin, polymyxin B, prontosil, pvampicillin, pyrazinamide, quinupristin/dalfopristin, rifampicin, rifampin, roxithromycin, sparfloxacin, spectinomycin, spiramycin, sulbactam, sulfacetamide, sulfamethizole, sulfamethoxazole, sulfanilimide, sulfisoxazole, sulphonamides, sultamicillin, telithromycin, tetracycline, thiamphenicol, ticarcillin, tobramycin, trimethoprim, trimethoprim-sulfamethoxazole, troleandomycin, trovafloxacin, or a combination thereof. In an aspect, an anti-bacterial agent can comprise a quinolone. In an aspect, a quinolone can comprise ciprofloxacin, enoxacin, gatifloxacin, gemifloxacin, grepafloxacin, levofloxacin, lomefloxacin, moxifloxacin, nalidixic acid, norfloxacin, ofloxacin, sparfloxacin, trovafloxacin, or a combination thereof. In an aspect, a quinolone can comprise levofloxacin. In an aspect, an anti-bacterial agent can comprise an aminoglycoside. In an aspect, an aminoglycoside can comprise amikacin, gentamicin, kanamycin, neomycin, streptomycin, tobramycin, or a combination thereof. In an aspect, an aminoglycoside can comprise tobramycin.

In an aspect, a container can be a glass container and can comprise a stopper or a seal. In an aspect, a container can be a non-glass container and can comprise a stopper or a seal. In an aspect, a stopper can comprise siliconized or non-siliconized rubber. In an aspect, rubber can be bromobutyl rubber or chlorobutyl rubber. In an aspect, a stopper or seal can comprise metal. In an aspect, a stopper or seal can comprise a Teflon coating or a Teflon treatment. In an aspect, a container can be a disposable packet. In an aspect, a disposable packet can be moisture-free. In an aspect, a container can be a glass or non-glass vial. In an aspect, a vial can be a 25 mL vial, a 50 mL vial, a 75 mL via, a 100 mL vial, a 125 mL vial, a 150 mL vial, a 175 mL vial, a 200 mL vial, a 250 mL vial, a 300 mL vial, a 350 mL vial, a 400 mL vial, a 450 mL vial, a 500 mL vial, or a 1000 mL vial. In an aspect, a vial can be range in size from about 25 mL to about 1000 mL. In an aspect, a vial can comprise a capsule or one or more capsules, each encapsulating a disclosed compounded composition.

3. Kits

Disclosed herein is a kit, comprising: a container comprising a compounded composition, wherein the compounded composition comprises a therapeutically effective amount of an anti-fungal agent and a sufficient amount of an excipient base powder comprising a blend of micronized xylitol and poloxamers. A disclosed compounded composition can comprise a dry powder formulation. In an aspect, a disclosed compounded composition can be encapsulated in a capsule or in one or more capsules.

In an aspect of a disclosed kit, an anti-infective agent can comprise an anti-fungal agent, an anti-bacterial agent, or a combination thereof. In an aspect, an anti-infective agent can comprise a dry powder and can be obtained from a bulk source.

In an aspect of a disclosed kit, an excipient base powder comprising a blend a micronized xylitol and poloxamers can be LoxaSperse™ excipient base powder. In an aspect, an excipient base powder comprising a blend a micronized xylitol and poloxamers can be XyliFos™ excipient base powder. In an aspect, XyliFos™ excipient base powder can comprise xylitol, poloxamer 407, hydroxylpropyl betadex, and epigallocatechin gallate. In an aspect, an excipient base powder can be obtained from a bulk source.

In an aspect of a disclosed kit, a kit can comprise instructions for using a compounded composition. In an aspect, a kit can comprise a foot bath. In an aspect, a foot bath can comprise a mechanical agitation agent to mechanically agitate the enclosed water, a heating agent to heat the enclosed water, or both. Mechanical agitation agents and/or means to agitate water within a compartment are known to the art. In an aspect, a mechanical agitation agent can be a motorized agitation agent. In an aspect, an agitation agent or an agitator can be coupled to both a motor and the foot bath. Motors and agitators are known to the art. In an aspect, mechanical agitation can serve to distribute the compounded composition throughout the water contained within the foot bath.

Heating agents and/or means to heat water in a compartment are known to the art.

In an aspect of a disclosed kit, an anti-fungal agent can comprise abafungin, albaconazole, amorolfin, amphotericin b, anidulafungin, bifonazole, butenafine, butoconazole, candicidin, caspofungin, ciclopirox, clotrimazole, econazole, fenticonazole, filipin, fluconazole, flucytosine, griseofulvin, haloprogin, hamycin, isavuconazole, isoconazole, itraconazole, ketoconazole, micafungin, miconazole, naftifine, natamycin, nystatin, omoconazole, oxiconazole, polygodial, posaconazole, ravuconazole, rimocidin, sertaconazole, sulconazole, terbinafine, terconazole, tioconazole, tolnaftate, undecylenic acid, voriconazole, or a combination thereof. In an aspect, an anti-fungal agent can comprise fluconazole, itraconazole, voriconazole, or a combination thereof. In an aspect, an anti-fungal agent can comprise fluconazole. In an aspect, an anti-fungal agent can comprise itraconazole or voriconazole or a combination thereof.

In an aspect, the ratio of an anti-fungal agent to excipient base powder in a disclosed compounded composition can be from about 1:60 to about 1:3. In an aspect, the ratio of an anti-fungal agent to excipient base powder in a disclosed compounded composition can be from about 1:60 to about 1:6. In an aspect, the ratio of an anti-fungal agent to excipient base powder in a disclosed compounded composition can be from about 1:30 to about 1:3. In an aspect, the ratio of an anti-fungal agent to excipient base powder in a disclosed compounded composition can be from about 1:20 to about 1:2. In an aspect, the ratio of an anti-fungal agent to excipient base powder in a disclosed compounded composition can be about 1:15. In an aspect, the amount of fluconazole in a disclosed compounded composition can be from about 200 mg to about 1000 mg and the amount of excipient base powder can be about 3 g. In an aspect, the amount of fluconazole in a disclosed compounded composition can be about 200 mg and the amount of excipient base powder can be about 3 g. In an aspect, the amount of fluconazole in a disclosed compounded composition can be about 1000 mg and the amount of excipient base powder can be about 3 g. In an aspect, the amount of itraconazole or voriconazole or a combination thereof in a disclosed compounded composition can be from about 50 mg to about 500 mg and the amount of excipient base powder can be about 3 g. In an aspect, the amount of itraconazole or voriconazole or a combination thereof in a disclosed compounded composition can be from about 200 mg and the amount of excipient base powder can be about 3 g.

In an aspect of a disclosed kit, a disclosed compounded composition can comprise one or more additional anti-infective agents. In an aspect, an additional anti-infective agent can comprise an anti-fungal agent, an anti-bacterial agent, or a combination thereof. In an aspect, an anti-infective agent can comprise a dry powder and can be obtained from a bulk source. In an aspect, the ratio of an additional anti-infective agent to excipient base powder in a disclosed compounded composition can be from about 1:60 to about 1:3. In an aspect, the ratio of an additional anti-infective agent to excipient base powder in a disclosed compounded composition can be from about 1:60 to about 1:6. In an aspect, the ratio of an additional anti-infective agent to excipient base powder in a disclosed compounded composition can be from about 1:30 to about 1:3. In an aspect, the ratio of an additional anti-infective agent to excipient base powder can be from about 1:20 to about 1:2. In an aspect, the ratio of additional anti-infective agent to excipient base powder can be about 1:15.

In an aspect of a disclosed kit, an anti-bacterial agent can comprise afenide, amikacin, amoxicillin, ampicillin, arsphenamine, azithromycin, azlocillin, aztreonam, bacampicillin, bacitracin, carbacephem (loracarbef), carbenicillin, cefaclor, cefadroxil, cefalotin, cefamandole, cefazolin, cefdinir, cefditoren, cefepime, cefixime, cefoperazone, cefotaxime, cefoxitin, cefpodoxime, cefprozil, ceftazidime, ceftibuten, ceftizoxime, ceftobiprole, ceftriaxone, cefuroxime, cephalexin, chloramphenicol, chlorhexidine, ciprofloxacin, clarithromycin, clavulanic acid, clindamycin, cloxacillin, colimycin, colistimethate teicoplanin, colistin, demeclocycline, dicloxacillin, dirithromycin, doripenem, doxycycline, efprozil, enoxacin, ertapenem, erythromycin, ethambutol, flucloxacillin, fosfomycin, furazolidone, gatifloxacin, geldanamycin, gemifloxacin, gentamicin, grepafloxacin, herbimycin, imipenem, isoniazid, kanamycin, levofloxacin, lincomycin, linezolid, lomefloxacin, meropenem, meticillin, metronidazole, mezlocillin, minocycline, mitomycin, moxifloxacin, mupirocin, nafcillin, neomycin, netilmicin, nitrofurantoin, norfloxacin, ofloxacin, oxacillin, oxytetracycline, paromomycin, penicillin G, penicillin V, piperacillin, pivmecillinam, platensimycin, polymyxin B, prontosil, pvampicillin, pyrazinamide, quinupristin/dalfopristin, rifampicin, rifampin, roxithromycin, sparfloxacin, spectinomycin, spiramycin, sulbactam, sulfacetamide, sulfamethizole, sulfamethoxazole, sulfanilimide, sulfisoxazole, sulphonamides, sultamicillin, telithromycin, tetracycline, thiamphenicol, ticarcillin, tobramycin, trimethoprim, trimethoprim-sulfamethoxazole, troleandomycin, trovafloxacin, or a combination thereof. In an aspect, an anti-bacterial agent can comprise a quinolone. In an aspect, a quinolone can comprise ciprofloxacin, enoxacin, gatifloxacin, gemifloxacin, grepafloxacin, levofloxacin, lomefloxacin, moxifloxacin, nalidixic acid, norfloxacin, ofloxacin, sparfloxacin, trovafloxacin, or a combination thereof. In an aspect, a quinolone can comprise levofloxacin. In an aspect, an anti-bacterial agent can comprise an aminoglycoside. In an aspect, an aminoglycoside can comprise amikacin, gentamicin, kanamycin, neomycin, streptomycin, tobramycin, or a combination thereof. In an aspect, an aminoglycoside can comprise tobramycin.

In an aspect of a disclosed kit, a container can be a glass container and can comprise a stopper or a seal. In an aspect, a container can be a non-glass container and can comprise a stopper or a seal. In an aspect, a stopper can comprise siliconized or non-siliconized rubber. In an aspect, rubber can be bromobutyl rubber or chlorobutyl rubber. In an aspect, a stopper or seal can comprise metal. In an aspect, a stopper or seal can comprise a Teflon coating or a Teflon treatment. In an aspect, a container can be a disposable packet. In an aspect, a disposable packet can be moisture-free. In an aspect, a container can be a glass or non-glass vial. In an aspect, a vial can be a 25 mL vial, a 50 mL vial, a 75 mL via, a 100 mL vial, a 125 mL vial, a 150 mL vial, a 175 mL vial, a 200 mL vial, a 250 mL vial, a 300 mL vial, a 350 mL vial, a 400 mL vial, a 450 mL vial, a 500 mL vial, or a 1000 mL vial. In an aspect, a vial can be range in size from about 25 mL to about 1000 mL. In an aspect, a vial can comprise a capsule or one or more capsules, each encapsulating a disclosed compounded composition.

Disclosed herein is a kit, comprising: a container comprising a compounded composition, wherein the compounded composition comprises a therapeutically effective amount of an anti-fungal agent and a sufficient amount of an excipient base powder comprising a blend of micronized xylitol and poloxamers, and instructions for using the compounded composition.

Disclosed herein is a kit, comprising: a container comprising a compounded composition, wherein the compounded composition comprises a therapeutically effective amount of an anti-fungal agent, a therapeutically effective amount of an anti-infective agent, and a sufficient amount of an excipient base powder comprising a blend of micronized xylitol and poloxamers, and instructions for using the compounded composition.

Disclosed herein is a kit, comprising: a container comprising a compounded composition, wherein the compounded composition comprises a therapeutically effective amount of an anti-fungal agent and a sufficient amount of an excipient base powder comprising a blend of micronized xylitol and poloxamers, a foot bath, and instructions for using the compounded composition.

Disclosed herein is a kit, comprising: a container comprising an anti-fungal agent, a container comprising an excipient base powder comprising a blend of micronized xylitol and poloxamers, and instructions for using the anti-fungal agent and the excipient base powder.

Disclosed herein is a kit, comprising: a container comprising an anti-fungal agent, a container comprising an excipient base powder comprising a blend of micronized xylitol and poloxamers, instructions for making a compounded composition comprising a therapeutically effective amount of the anti-fungal agent and a sufficient amount of the excipient base powder, and instructions for using the compounded composition.

Disclosed herein is a kit, comprising: a container comprising an anti-fungal agent, a container comprising an excipient base powder comprising a blend of micronized xylitol and poloxamers, instructions for making a compounded composition comprising a therapeutically effective amount of the anti-fungal agent and a sufficient amount of the excipient base powder, a foot bath, and instructions for using the compounded composition.

Disclosed herein is a kit, comprising: a container comprising an anti-fungal agent, a container comprising an anti-infective agent, a container comprising an excipient base powder comprising a blend of micronized xylitol and poloxamers, instructions for making a compounded composition comprising a therapeutically effective amount of the anti-fungal agent, a therapeutically effective amount of the anti-infective agent, and a sufficient amount of the excipient base powder, a foot bath, and instructions for using the compounded composition.

Disclosed herein is a kit, comprising: a container comprising a compounded composition, wherein the compounded composition comprises a therapeutically effective amount of fluconazole and a sufficient amount of an excipient base powder comprising a blend of micronized xylitol and poloxamers, and instructions for using the compounded composition.

Disclosed herein is a kit, comprising: a container comprising a compounded composition, wherein the compounded composition comprises a therapeutically effective amount of fluconazole, a therapeutically effective amount of an anti-infective agent, and a sufficient amount of an excipient base powder comprising a blend of micronized xylitol and poloxamers, and instructions for using the compounded composition.

Disclosed herein is a kit, comprising: a container comprising a compounded composition, wherein the compounded composition comprises a therapeutically effective amount of fluconazole and a sufficient amount of an excipient base powder comprising a blend of micronized xylitol and poloxamers, a foot bath, and instructions for using the compounded composition.

Disclosed herein is a kit, comprising: a container comprising fluconazole, a container comprising an excipient base powder comprising a blend of micronized xylitol and poloxamers, and instructions for using the anti-fungal agent and the excipient base powder.

Disclosed herein is a kit, comprising: a container comprising fluconazole, a container comprising an excipient base powder comprising a blend of micronized xylitol and poloxamers, instructions for making a compounded composition comprising a therapeutically effective amount of the anti-fungal agent and a sufficient amount of the excipient base powder, and instructions for using the compounded composition.

Disclosed herein is a kit, comprising: a container comprising fluconazole, a container comprising an excipient base powder comprising a blend of micronized xylitol and poloxamers, instructions for making a compounded composition comprising a therapeutically effective amount of fluconazole and a sufficient amount of the excipient base powder, a foot bath, and instructions for using the compounded composition.

Disclosed herein is a kit, comprising: a container comprising fluconazole, a container comprising an anti-infective agent, a container comprising an excipient base powder comprising a blend of micronized xylitol and poloxamers, instructions for making a compounded composition comprising a therapeutically effective amount of fluconazole, a therapeutically effective amount of the anti-infective agent, and a sufficient amount of the excipient base powder, a foot bath, and instructions for using the compounded composition.

In an aspect of a disclosed kit, an anti-infective agent can comprise an anti-fungal agent, an anti-bacterial agent, or a combination thereof. In an aspect, an anti-infective agent can comprise a dry powder and can be obtained from a bulk source.

In an aspect of a disclosed kit, an excipient base powder comprising a blend a micronized xylitol and poloxamers can be LoxaSperse™ excipient base powder. In an aspect, an excipient base powder comprising a blend a micronized xylitol and poloxamers can be XyliFos™ excipient base powder. In an aspect, XyliFos™ excipient base powder can comprise xylitol, poloxamer 407, hydroxylpropyl betadex, and epigallocatechin gallate. In an aspect, an excipient base powder can be obtained from a bulk source.

In an aspect of a disclosed kit, a kit can comprise instructions for using a compounded composition. In an aspect, a kit can comprise a foot bath. In an aspect, a foot bath can comprise a mechanical agitation agent to mechanically agitate the enclosed water, a heating agent to heat the enclosed water, or both. Mechanical agitation agents and/or means to agitate water in a compartment are known to the art. In as aspect, a mechanical agitation agent can be a motorized agitation agent. In an aspect, an agitation agent or an agitator can be coupled to both a motor and the foot bath. Motors and agitators are known to the art. In an aspect, mechanical agitation can serve to distribute the compounded composition throughout the water contained within the foot bath. Heating agents and/or means to heat water in a compartment are known to the art.

In an aspect of a disclosed kit, an anti-fungal agent can comprise abafungin, albaconazole, amorolfin, amphotericin b, anidulafungin, bifonazole, butenafine, butoconazole, candicidin, caspofungin, ciclopirox, clotrimazole, econazole, fenticonazole, filipin, fluconazole, flucytosine, griseofulvin, haloprogin, hamycin, isavuconazole, isoconazole, itraconazole, ketoconazole, micafungin, miconazole, naftifine, natamycin, nystatin, omoconazole, oxiconazole, polygodial, posaconazole, ravuconazole, rimocidin, sertaconazole, sulconazole, terbinafine, terconazole, tioconazole, tolnaftate, undecylenic acid, voriconazole, or a combination thereof. In an aspect, an anti-fungal agent can comprise fluconazole, itraconazole, voriconazole, or a combination thereof. In an aspect, an anti-fungal agent can comprise fluconazole. In an aspect, an anti-fungal agent can comprise itraconazole or voriconazole or a combination thereof.

In an aspect, the ratio of an anti-fungal agent to excipient base powder in a disclosed compounded composition can be from about 1:60 to about 1:3. In an aspect, the ratio of an anti-fungal agent to excipient base powder in a disclosed compounded composition can be from about 1:60 to about 1:6. In an aspect, the ratio of an anti-fungal agent to excipient base powder in a disclosed compounded composition can be from about 1:30 to about 1:3. In an aspect, the ratio of an anti-fungal agent to excipient base powder in a disclosed compounded composition can be from about 1:20 to about 1:2. In an aspect, the ratio of an anti-fungal agent to excipient base powder in a disclosed compounded composition can be about 1:15. In an aspect, the amount of fluconazole in a disclosed compounded composition can be from about 200 mg to about 1000 mg and the amount of excipient base powder can be about 3 g. In an aspect, the amount of fluconazole in a disclosed compounded composition can be about 200 mg and the amount of excipient base powder can be about 3 g. In an aspect, the amount of fluconazole in a disclosed compounded composition can be about 1000 mg and the amount of excipient base powder can be about 3 g. In an aspect, the amount of itraconazole or voriconazole or a combination thereof in a disclosed compounded composition can be from about 50 mg to about 500 mg and the amount of excipient base powder can be about 3 g. In an aspect, the amount of itraconazole or voriconazole or a combination thereof in a disclosed compounded composition can be from about 200 mg and the amount of excipient base powder can be about 3 g.

In an aspect of a disclosed kit, a disclosed compounded composition can comprise one or more additional anti-infective agents. In an aspect, an additional anti-infective agent can comprise an anti-fungal agent, an anti-bacterial agent, or a combination thereof. In an aspect, an anti-infective agent can comprise a dry powder and can be obtained from a bulk source. In an aspect, the ratio of an additional anti-infective agent to excipient base powder in a disclosed compounded composition can be from about 1:60 to about 1:3. In an aspect, the ratio of an additional anti-infective agent to excipient base powder in a disclosed compounded composition can be from about 1:60 to about 1:6. In an aspect, the ratio of an additional anti-infective agent to excipient base powder in a disclosed compounded composition can be from about 1:30 to about 1:3. In an aspect, the ratio of an additional anti-infective agent to excipient base powder can be from about 1:20 to about 1:2. In an aspect, the ratio of additional anti-infective agent to excipient base powder can be about 1:15.

In an aspect of a disclosed kit, an anti-bacterial agent can comprise afenide, amikacin, amoxicillin, ampicillin, arsphenamine, azithromycin, azlocillin, aztreonam, bacampicillin, bacitracin, carbacephem (loracarbef), carbenicillin, cefaclor, cefadroxil, cefalotin, cefamandole, cefazolin, cefdinir, cefditoren, cefepime, cefixime, cefoperazone, cefotaxime, cefoxitin, cefpodoxime, cefprozil, ceftazidime, ceftibuten, ceftizoxime, ceftobiprole, ceftriaxone, cefuroxime, cephalexin, chloramphenicol, chlorhexidine, ciprofloxacin, clarithromycin, clavulanic acid, clindamycin, cloxacillin, colimycin, colistimethate teicoplanin, colistin, demeclocycline, dicloxacillin, dirithromycin, doripenem, doxycycline, efprozil, enoxacin, ertapenem, erythromycin, ethambutol, flucloxacillin, fosfomycin, furazolidone, gatifloxacin, geldanamycin, gemifloxacin, gentamicin, grepafloxacin, herbimycin, imipenem, isoniazid, kanamycin, levofloxacin, lincomycin, linezolid, lomefloxacin, meropenem, meticillin, metronidazole, mezlocillin, minocycline, mitomycin, moxifloxacin, mupirocin, nafcillin, neomycin, netilmicin, nitrofurantoin, norfloxacin, ofloxacin, oxacillin, oxytetracycline, paromomycin, penicillin G, penicillin V, piperacillin, pivmecillinam, platensimycin, polymyxin B, prontosil, pvampicillin, pyrazinamide, quinupristin/dalfopristin, rifampicin, rifampin, roxithromycin, sparfloxacin, spectinomycin, spiramycin, sulbactam, sulfacetamide, sulfamethizole, sulfamethoxazole, sulfanilimide, sulfisoxazole, sulphonamides, sultamicillin, telithromycin, tetracycline, thiamphenicol, ticarcillin, tobramycin, trimethoprim, trimethoprim-sulfamethoxazole, troleandomycin, trovafloxacin, or a combination thereof. In an aspect, an anti-bacterial agent can comprise a quinolone. In an aspect, a quinolone can comprise ciprofloxacin, enoxacin, gatifloxacin, gemifloxacin, grepafloxacin, levofloxacin, lomefloxacin, moxifloxacin, nalidixic acid, norfloxacin, ofloxacin, sparfloxacin, trovafloxacin, or a combination thereof. In an aspect, a quinolone can comprise levofloxacin. In an aspect, an anti-bacterial agent can comprise an aminoglycoside. In an aspect, an aminoglycoside can comprise amikacin, gentamicin, kanamycin, neomycin, streptomycin, tobramycin, or a combination thereof. In an aspect, an aminoglycoside can comprise tobramycin.

In an aspect of a disclosed kit, a container can be a glass container and can comprise a stopper or a seal. In an aspect, a container can be a non-glass container and can comprise a stopper or a seal. In an aspect, a stopper can comprise siliconized or non-siliconized rubber. In an aspect, rubber can be bromobutyl rubber or chlorobutyl rubber. In an aspect, a stopper or seal can comprise metal. In an aspect, a stopper or seal can comprise a Teflon coating or a Teflon treatment. In an aspect, a container can be a disposable packet. In an aspect, a disposable packet can be moisture-free. In an aspect, a container can be a glass or non-glass vial. In an aspect, a vial can be a 25 mL vial, a 50 mL vial, a 75 mL via, a 100 mL vial, a 125 mL vial, a 150 mL vial, a 175 mL vial, a 200 mL vial, a 250 mL vial, a 300 mL vial, a 350 mL vial, a 400 mL vial, a 450 mL vial, a 500 mL vial, or a 1000 mL vial. In an aspect, a vial can be range in size from about 25 mL to about 1000 mL. In an aspect, a vial can comprise one or more capsules, encapsulating a disclosed compounded composition.

C. Methods

1. Methods of Treating of Preventing a Fungal Infection

Disclosed herein is a method of treating or preventing a fungal infection in a subject, the method comprising: (i) adding to water contained within a foot bath a compounded composition comprising fluconazole and LoxaSperse™ excipient base powder; (ii) agitating the water using an agitator, thereby distributing the compounded composition throughout the water; and (iii) contacting the agitated water with at least a portion of one or both feet of a subject, wherein the subject has been diagnosed with, is suspected of having, or is at risk of developing a fungal infection.

Disclosed herein is a method of treating or preventing a fungal infection, the method comprising: (i) adding to water contained within a foot bath a compounded composition comprising an anti-fungal agent and an excipient base powder comprising a blend of micronized xylitol and poloxamers; (ii) agitating the water contained within the foot bath; and (iii) contacting the agitated water with at least a portion of one or both feet of a subject.

Disclosed herein is a method of treating or preventing a fungal infection, the method comprising: (i) adding any compounded composition disclosed herein to water contained within a foot bath; (ii) agitating the water contained within the foot bath; and (iii) contacting the agitated water with at least a portion of one or both feet of a subject.

Figure 3:
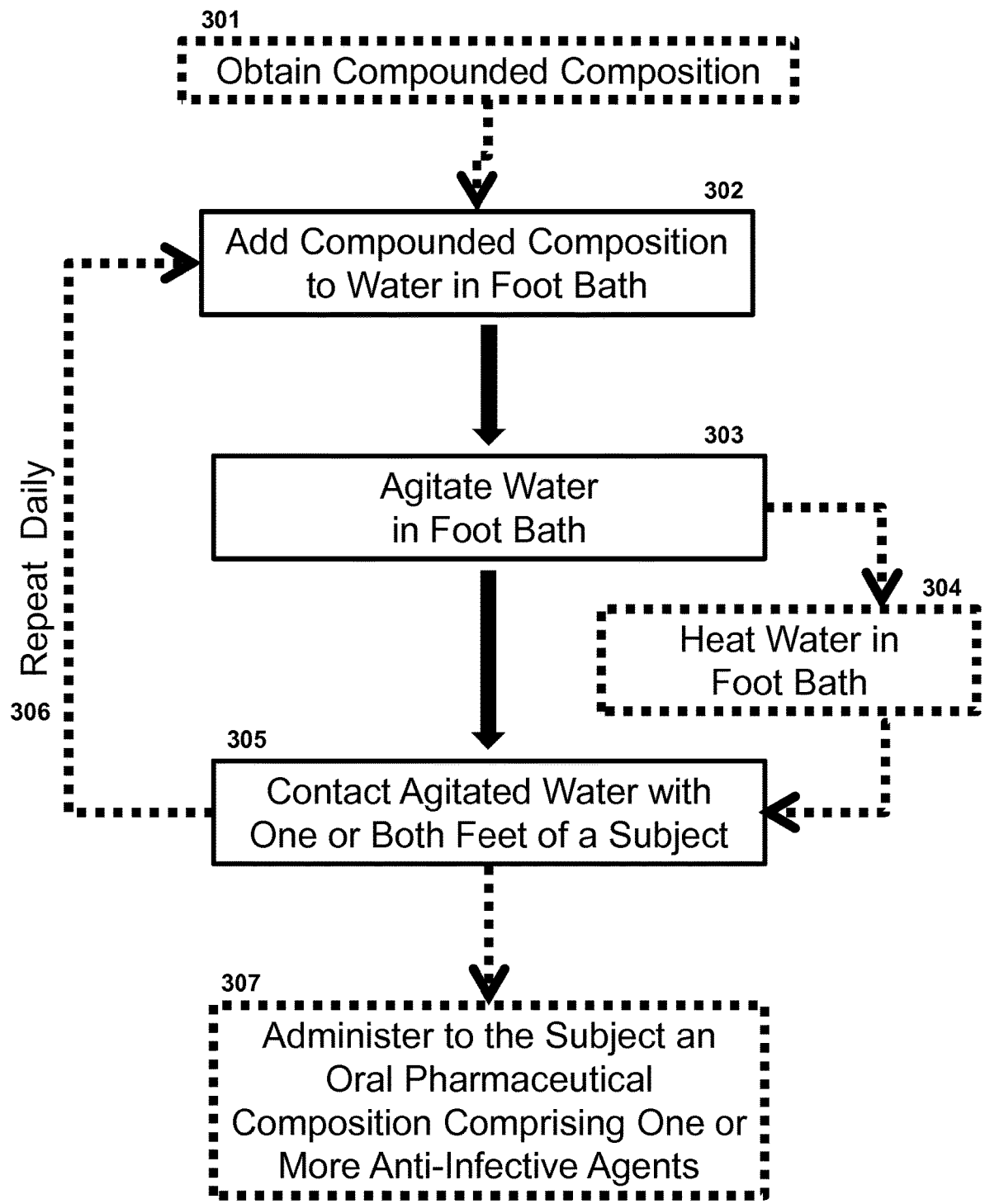
FIG. 3 shows a schematic of a disclosed method of treating or preventing of fungal infection.

Disclosed herein is a method of treating or preventing a fungal infection, the method comprising: (i) adding a compounded composition to water contained within a foot bath (302); (ii) agitating the water contained within the foot bath (303); and (iii) contacting the agitated water with at least a portion of one or both feet of a subject (305). See, e.g., FIG. 3, in which the hatched boxes and lines represent steps of a disclosed method that are optionally performed.

In an aspect of a disclosed method, a subject can be diagnosed with or can be suspected of having a fungal infection of at least a portion of one or both feet. In an aspect, a subject can have diabetes. In an aspect, a subject can be obese. In an aspect, a subject can have circulatory issues. In an aspect, a subject can be at risk of developing a fungal infection. For example, an at-risk subject can have damaged or moist skin, can have chronic disease, or can be immunocompromised.

In an aspect, a disclosed method can comprise obtaining a compounded composition (301).

In an aspect of a disclosed method, contacting the agitated water with at least a portion of one or both feet of a subject can comprise placing at least a portion of one or both feet of the subject in the foot bath. In an aspect, contacting the agitated water with at least a portion of one or both feet of a subject can comprise placing at least a portion of one or both feet of the subject in the foot bath for about 5 minutes to about 30 minutes. In an aspect, contacting the agitated water with at least a portion of one or both feet of a subject can comprise placing at least a portion of one or both feet of the subject in the foot bath for about 5 to about 20 minutes. In an aspect, contacting the agitated water with at least a portion of one or both feet of a subject can comprise placing at least a portion of one or both feet of the subject in the foot bath for about 10 minutes.

In an aspect, a method of treating or preventing a fungal infection can comprise repeating steps (i)-(iii) daily (306). In an aspect, a method of treating or preventing a fungal infection can comprise repeating steps (i)-(iii) daily until the fungal infection or suspected fungal infection is eradicated.

In an aspect, a method of treating or preventing a fungal infection can comprise heating the water contained within the foot bath (304).

In an aspect of a disclosed method of treating or preventing a fungal infection, a compounded composition can comprise an anti-fungal agent and an excipient base powder comprising a blend of micronized xylitol and poloxamers. In an aspect, a disclosed compounded composition can be a dry powder formulation. In an aspect, a disclosed compounded composition can be encapsulated in a capsule or in one or more capsules. In an aspect, an anti-fungal agent can comprise a dry powder and can be obtained from a bulk source.

In an aspect of a disclosed method, an excipient base powder comprising a blend a micronized xylitol and poloxamers can be LoxaSperse™ excipient base powder. In an aspect, an excipient base powder comprising a blend a micronized xylitol and poloxamers can be XyliFos™ excipient base powder. In an aspect, XyliFos™ excipient base powder can comprise xylitol, poloxamer 407, hydroxypropyl betadex, and epigallocatechin gallate. In an aspect, an excipient base powder can be obtained from a bulk source.

In an aspect of a disclosed method, an anti-fungal agent of a disclosed compounded composition can comprise abafungin, albaconazole, amorolfin, amphotericin b, anidulafungin, bifonazole, butenafine, butoconazole, candicidin, caspofungin, ciclopirox, clotrimazole, econazole, fenticonazole, filipin, fluconazole, flucytosine, griseofulvin, haloprogin, hamycin, isavuconazole, isoconazole, itraconazole, ketoconazole, micafungin, miconazole, naftifine, natamycin, nystatin, omoconazole, oxiconazole, polygodial, posaconazole, ravuconazole, rimocidin, sertaconazole, sulconazole, terbinafine, terconazole, tioconazole, tolnaftate, undecylenic acid, voriconazole, or a combination thereof. In an aspect, an anti-fungal agent can comprise fluconazole, itraconazole, voriconazole, or a combination thereof. In an aspect, an anti-fungal agent can comprise fluconazole. In an aspect, an anti-fungal agent can comprise itraconazole or voriconazole.

In an aspect, the ratio of an anti-fungal agent to excipient base powder in a disclosed compounded composition can be from about 1:60 to about 1:3. In an aspect, the ratio of an anti-fungal agent to excipient base powder in a disclosed compounded composition can be from about 1:60 to about 1:6. In an aspect, the ratio of an anti-fungal agent to excipient base powder in a disclosed compounded composition can be from about 1:30 to about 1:3. In an aspect, the ratio of an anti-fungal agent to excipient base powder in a disclosed compounded composition can be from about 1:20 to about 1:2. In an aspect, the ratio of an anti-fungal agent to excipient base powder in a disclosed compounded composition can be about 1:15. In an aspect, the amount of fluconazole in a disclosed compounded composition can be from about 200 mg to about 1000 mg and the amount of excipient base powder can be about 3 g. In an aspect, the amount of fluconazole in a disclosed compounded composition can be about 200 mg and the amount of excipient base powder can be about 3 g. In an aspect, the amount of fluconazole in a disclosed compounded composition can be about 1000 mg and the amount of excipient base powder can be about 3 g. In an aspect, the amount of itraconazole or voriconazole or a combination thereof in a disclosed compounded composition can be from about 50 mg to about 500 mg and the amount of excipient base powder can be about 3 g. In an aspect, the amount of itraconazole or voriconazole or a combination thereof in a disclosed compounded composition can be from about 200 mg and the amount of excipient base powder can be about 3 g.

In an aspect of a disclosed method, a compounded composition can comprise one or more additional anti-infective agents. In an aspect, an additional anti-infective agent can comprise an anti-fungal agent, an anti-bacterial agent, or a combination thereof. In an aspect, an anti-infective agent can comprise a dry powder and can be obtained from a bulk source. In an aspect, the ratio of an additional anti-infective agent to excipient base powder in a disclosed compounded composition can be from about 1:60 to about 1:3. In an aspect, the ratio of an additional anti-infective agent to excipient base powder in a disclosed compounded composition can be from about 1:60 to about 1:6. In an aspect, the ratio of an additional anti-infective agent to excipient base powder in a disclosed compounded composition can be from about 1:30 to about 1:3. In an aspect, the ratio of an additional anti-infective agent to excipient base powder can be from about 1:20 to about 1:2. In an aspect, the ratio of an additional anti-infective agent to excipient base powder can be about 1:15.

In an aspect of a disclosed method, an anti-bacterial agent can comprise afenide, amikacin, amoxicillin, ampicillin, arsphenamine, azithromycin, azlocillin, aztreonam, bacampicillin, bacitracin, carbacephem (loracarbef), carbenicillin, cefaclor, cefadroxil, cefalotin, cefamandole, cefazolin, cefdinir, cefditoren, cefepime, cefixime, cefoperazone, cefotaxime, cefoxitin, cefpodoxime, cefprozil, ceftazidime, ceftibuten, ceftizoxime, ceftobiprole, ceftriaxone, cefuroxime, cephalexin, chloramphenicol, chlorhexidine, ciprofloxacin, clarithromycin, clavulanic acid, clindamycin, cloxacillin, colimycin, colistimethate teicoplanin, colistin, demeclocycline, dicloxacillin, dirithromycin, doripenem, doxycycline, efprozil, enoxacin, ertapenem, erythromycin, ethambutol, flucloxacillin, fosfomycin, furazolidone, gatifloxacin, geldanamycin, gemifloxacin, gentamicin, grepafloxacin, herbimycin, imipenem, isoniazid, kanamycin, levofloxacin, lincomycin, linezolid, lomefloxacin, meropenem, meticillin, metronidazole, mezlocillin, minocycline, mitomycin, moxifloxacin, mupirocin, nafcillin, neomycin, netilmicin, nitrofurantoin, norfloxacin, ofloxacin, oxacillin, oxytetracycline, paromomycin, penicillin G, penicillin V, piperacillin, pivmecillinam, platensimycin, polymyxin B, prontosil, pvampicillin, pyrazinamide, quinupristin/dalfopristin, rifampicin, rifampin, roxithromycin, sparfloxacin, spectinomycin, spiramycin, sulbactam, sulfacetamide, sulfamethizole, sulfamethoxazole, sulfanilimide, sulfisoxazole, sulphonamides, sultamicillin, telithromycin, tetracycline, thiamphenicol, ticarcillin, tobramycin, trimethoprim, trimethoprim-sulfamethoxazole, troleandomycin, trovafloxacin, or a combination thereof. In an aspect, an anti-bacterial agent can comprise a quinolone. In an aspect, a quinolone can comprise ciprofloxacin, enoxacin, gatifloxacin, gemifloxacin, grepafloxacin, levofloxacin, lomefloxacin, moxifloxacin, nalidixic acid, norfloxacin, ofloxacin, sparfloxacin, trovafloxacin, or a combination thereof. In an aspect, a quinolone can comprise levofloxacin. In an aspect, an anti-bacterial agent can comprise an aminoglycoside. In an aspect, an aminoglycoside can comprise amikacin, gentamicin, kanamycin, neomycin, streptomycin, tobramycin, or a combination thereof. In an aspect, an aminoglycoside can comprise tobramycin.

In an aspect of a disclosed method, a container can be a glass container and can comprise a stopper or a seal. In an aspect, a container can be a non-glass container and can comprise a stopper or a seal. In an aspect, a stopper can comprise siliconized or non-siliconized rubber. In an aspect, rubber can be bromobutyl rubber or chlorobutyl rubber. In an aspect, a stopper or seal can comprise metal. In an aspect, a stopper or seal can comprise a Teflon coating or a Teflon treatment. In an aspect, a container can be a disposable packet. In an aspect, a disposable packet can be moisture-free. In an aspect, a container can be a glass or non-glass vial. In an aspect, a vial can be a 25 mL vial, a 50 mL vial, a 75 mL via, a 100 mL vial, a 125 mL vial, a 150 mL vial, a 175 mL vial, a 200 mL vial, a 250 mL vial, a 300 mL vial, a 350 mL vial, a 400 mL vial, a 450 mL vial, a 500 mL vial, or a 1000 mL vial. In an aspect, a vial can be range in size from about 25 mL to about 1000 mL. In an aspect, a vial can comprise a capsule or one or more capsules, each encapsulating a disclosed compounded composition.

In an aspect, a method of treating or preventing a fungal infection can comprise administering to the subject an oral pharmaceutical composition comprising one or more anti-infective agents. In an aspect, a method of treating or preventing a fungal infection can comprise administering to the subject an oral pharmaceutical composition comprising an anti-infective agent. In an aspect, a method of treating or preventing a fungal infection can comprise administering to the subject an oral pharmaceutical composition comprising an anti-fungal agent. In an aspect, a method of treating or preventing a fungal infection method can comprise administering to the subject an oral pharmaceutical composition comprising an anti-bacterial agent (307).

In an aspect, a disclosed method can be prophylactic, therapeutic, or both. As a prophylactic, a subject performs a disclosed method prior to onset (e.g., before developing a fungal infection) or during early onset (e.g., upon initial signs and symptoms of a fungal infection). In an aspect, as a prophylactic, a subject performs a disclosed method for a period of time prior to the manifestation of symptoms of a fungal infection. As a prophylactic, a disclosed method can be performed by a subject at risk of developing a fungal infection. As a therapeutic, a subject, for example, a subject diagnosed with a fungal infection, can perform a disclosed method so as to treat an active fungal infection.

In an aspect, a disclosed method can treat or prevent a fungal infection affecting the skin of at least a portion of a subject's foot or feet. In an aspect, a disclosed method can treat or prevent a fungal infection affecting the nail of at least one toe on a subject's foot or feet.

Figure 4:
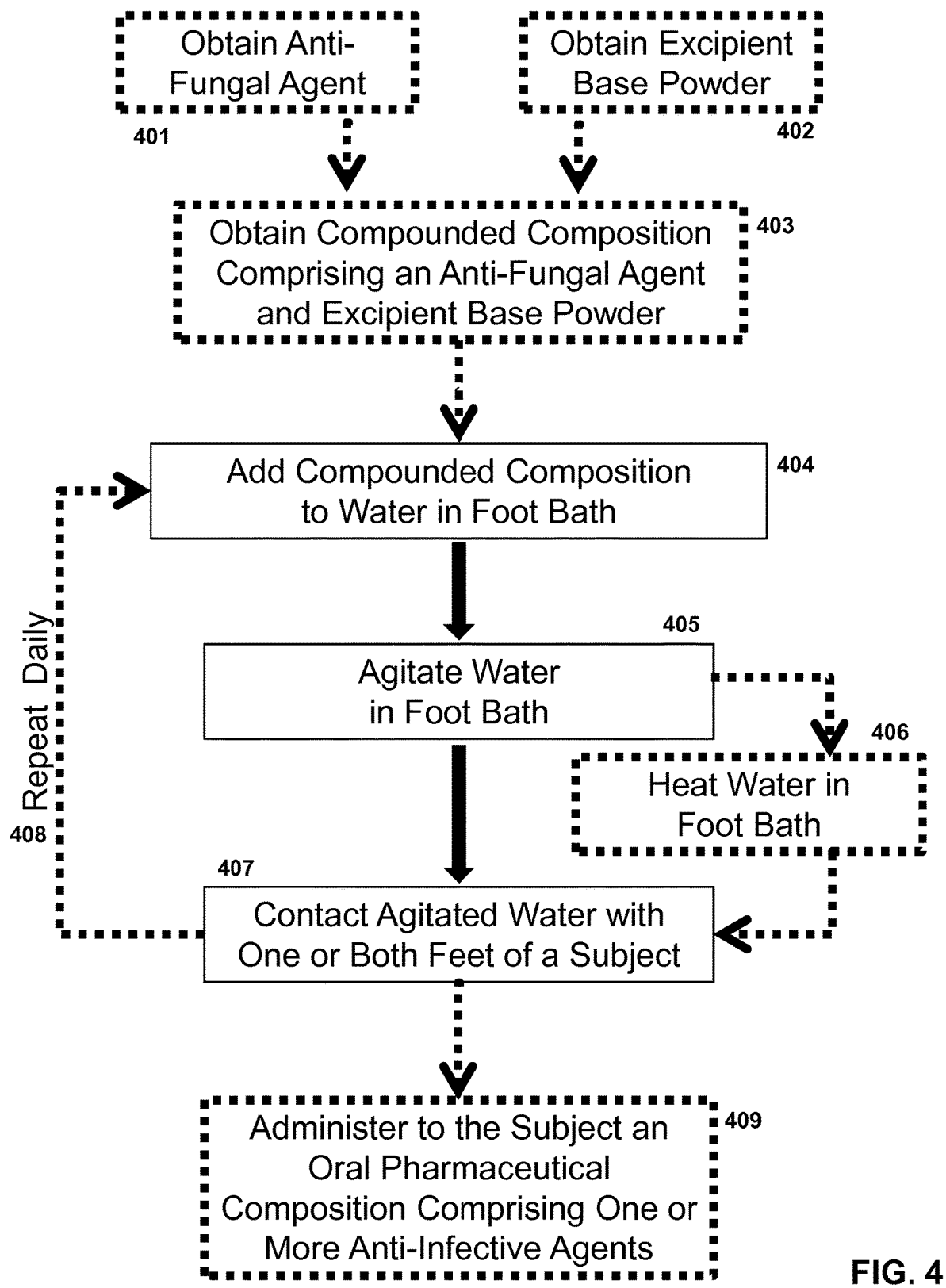
FIG. 4 shows a schematic of a disclosed method of treating or preventing of fungal infection.

Disclosed herein is a method of treating or preventing a fungal infection, the method comprising: (i) adding to water contained within a foot bath a compounded composition comprising an anti-fungal agent and an excipient base powder comprising a blend a micronized xylitol and poloxamers (404); (ii) agitating the water contained within the foot bath (405); and (iii) contacting the agitated water with at least a portion of one or both feet of a subject (407). See FIG. 4, in which the hatched boxes and lines represent steps of the method are optionally performed.

In an aspect of a disclosed method, a subject can be diagnosed with or can be suspected of having a fungal infection of at least a portion of one or both feet. In an aspect, a subject can have diabetes. In an aspect, a subject can be obese. In an aspect, a subject can have circulatory issues. In an aspect, a subject can be at risk of developing a fungal infection. For example, an at-risk subject can have damaged or moist skin, can have chronic disease, or can be immunocompromised.

In an aspect, a disclosed method can comprise obtaining a compounded composition (403). In an aspect, obtaining a compounded composition can comprise obtaining an anti-fungal agent (401) and an excipient base powder (402), or a combination thereof. In an aspect, obtaining an anti-fungal agent, one or more anti-infective agents, and an excipient base powder can comprise obtaining a bulk source of an anti-fungal agent, one or more anti-infective agents, or a combination thereof.

In an aspect, a method of treating or preventing a fungal infection can comprise heating the water contained within the foot bat (406).

In an aspect of a disclosed method, contacting the agitated water with at least a portion of one or both feet of a subject can comprise placing at least a portion of one or both feet of the subject in the foot bath. In an aspect, contacting the agitated water with at least a portion of one or both feet of a subject can comprise placing at least a portion of one or both feet of the subject in the foot bath for about 5 minutes to about 30 minutes. In an aspect, contacting the agitated water with at least a portion of one or both feet of a subject can comprise placing at least a portion of one or both feet of the subject in the foot bath for about 5 to about 20 minutes. In an aspect, contacting the agitated water with at least a portion of one or both feet of a subject can comprise placing at least a portion of one or both feet of the subject in the foot bath for about 10 minutes.

In an aspect, a compounded composition can be a dry powder formulation. In an aspect, a disclosed compounded composition can be encapsulated in a capsule or in one or more capsules. In an aspect, an anti-fungal agent can comprise a dry powder and can be obtained from a bulk source.

In an aspect of a disclosed method, an excipient base powder comprising a blend a micronized xylitol and poloxamers can be LoxaSperse™ excipient base powder. In an aspect, an excipient base powder comprising a blend a micronized xylitol and poloxamers can be XyliFos™ excipient base powder. In an aspect, XyliFos™ excipient base powder can comprise xylitol, poloxamer 407, hydroxylpropyl betadex, and epigallocatechin gallate. In an aspect, an excipient base powder can be obtained from a bulk source.

In an aspect of a disclosed method, an anti-fungal agent of a disclosed compounded composition can comprise abafungin, albaconazole, amorolfin, amphotericin b, anidulafungin, bifonazole, butenafine, butoconazole, candicidin, caspofungin, ciclopirox, clotrimazole, econazole, fenticonazole, filipin, fluconazole, flucytosine, griseofulvin, haloprogin, hamycin, isavuconazole, isoconazole, itraconazole, ketoconazole, micafungin, miconazole, naftifine, natamycin, nystatin, omoconazole, oxiconazole, polygodial, posaconazole, ravuconazole, rimocidin, sertaconazole, sulconazole, terbinafine, terconazole, tioconazole, tolnaftate, undecylenic acid, voriconazole, or a combination thereof. In an aspect, an anti-fungal agent can comprise fluconazole, itraconazole, voriconazole, or a combination thereof. In an aspect, an anti-fungal agent can comprise fluconazole. In an aspect, an anti-fungal agent can comprise itraconazole or voriconazole or a combination thereof.

In an aspect, the ratio of an anti-fungal agent to excipient base powder in a disclosed compounded composition can be from about 1:60 to about 1:3. In an aspect, the ratio of an anti-fungal agent to excipient base powder in a disclosed compounded composition can be from about 1:60 to about 1:6. In an aspect, the ratio of an anti-fungal agent to excipient base powder in a disclosed compounded composition can be from about 1:30 to about 1:3. In an aspect, the ratio of an anti-fungal agent to excipient base powder in a disclosed compounded composition can be from about 1:20 to about 1:2. In an aspect, the ratio of an anti-fungal agent to excipient base powder in a disclosed compounded composition can be about 1:15. In an aspect, the amount of fluconazole in a disclosed compounded composition can be from about 200 mg to about 1000 mg and the amount of excipient base powder can be about 3 g. In an aspect, the amount of fluconazole in a disclosed compounded composition can be about 200 mg and the amount of excipient base powder can be about 3 g. In an aspect, the amount of fluconazole in a disclosed compounded composition can be about 1000 mg and the amount of excipient base powder can be about 3 g. In an aspect, the amount of itraconazole or voriconazole or a combination thereof in a disclosed compounded composition can be from about 50 mg to about 500 mg and the amount of excipient base powder can be about 3 g. In an aspect, the amount of itraconazole or voriconazole or a combination thereof in a disclosed compounded composition can be from about 200 mg and the amount of excipient base powder can be about 3 g.

In an aspect, a method of treating or preventing a fungal infection can comprise repeating steps (i)-(iii) daily (408). In an aspect, a method of treating or preventing a fungal infection can comprise repeating steps (i)-(iii) daily until the fungal infection or suspected fungal infection is eradicated.

In an aspect of a disclosed method, a compounded composition can comprise one or more additional anti-infective agents. In an aspect, an additional anti-infective agent can comprise an anti-fungal agent, an anti-bacterial agent, or a combination thereof. In an aspect, an anti-infective agent can comprise a dry powder and can be obtained from a bulk source. In an aspect, the ratio of an additional anti-infective agent to excipient base powder in a disclosed compounded composition can be from about 1:60 to about 1:3. In an aspect, the ratio of an additional anti-infective agent to excipient base powder in a disclosed compounded composition can be from about 1:60 to about 1:6. In an aspect, the ratio of an additional anti-infective agent to excipient base powder in a disclosed compounded composition can be from about 1:30 to about 1:3. In an aspect, the ratio of an additional anti-infective agent to excipient base powder can be from about 1:20 to about 1:2. In an aspect, the ratio of additional anti-infective agent to excipient base powder can be about 1:15.

In an aspect of a disclosed method, an anti-bacterial agent can comprise afenide, amikacin, amoxicillin, ampicillin, arsphenamine, azithromycin, azlocillin, aztreonam, bacampicillin, bacitracin, carbacephem (loracarbef), carbenicillin, cefaclor, cefadroxil, cefalotin, cefamandole, cefazolin, cefdinir, cefditoren, cefepime, cefixime, cefoperazone, cefotaxime, cefoxitin, cefpodoxime, cefprozil, ceftazidime, ceftibuten, ceftizoxime, ceftobiprole, ceftriaxone, cefuroxime, cephalexin, chloramphenicol, chlorhexidine, ciprofloxacin, clarithromycin, clavulanic acid, clindamycin, cloxacillin, colimycin, colistimethate teicoplanin, colistin, demeclocycline, dicloxacillin, dirithromycin, doripenem, doxycycline, efprozil, enoxacin, ertapenem, erythromycin, ethambutol, flucloxacillin, fosfomycin, furazolidone, gatifloxacin, geldanamycin, gemifloxacin, gentamicin, grepafloxacin, herbimycin, imipenem, isoniazid, kanamycin, levofloxacin, lincomycin, linezolid, lomefloxacin, meropenem, meticillin, metronidazole, mezlocillin, minocycline, mitomycin, moxifloxacin, mupirocin, nafcillin, neomycin, netilmicin, nitrofurantoin, norfloxacin, ofloxacin, oxacillin, oxytetracycline, paromomycin, penicillin G, penicillin V, piperacillin, pivmecillinam, platensimycin, polymyxin B, prontosil, pvampicillin, pyrazinamide, quinupristin/dalfopristin, rifampicin, rifampin, roxithromycin, sparfloxacin, spectinomycin, spiramycin, sulbactam, sulfacetamide, sulfamethizole, sulfamethoxazole, sulfanilimide, sulfisoxazole, sulphonamides, sultamicillin, telithromycin, tetracycline, thiamphenicol, ticarcillin, tobramycin, trimethoprim, trimethoprim-sulfamethoxazole, troleandomycin, trovafloxacin, or a combination thereof. In an aspect, an anti-bacterial agent can comprise a quinolone. In an aspect, a quinolone can comprise ciprofloxacin, enoxacin, gatifloxacin, gemifloxacin, grepafloxacin, levofloxacin, lomefloxacin, moxifloxacin, nalidixic acid, norfloxacin, ofloxacin, sparfloxacin, trovafloxacin, or a combination thereof. In an aspect, a quinolone can comprise levofloxacin. In an aspect, an anti-bacterial agent can comprise an aminoglycoside. In an aspect, an aminoglycoside can comprise amikacin, gentamicin, kanamycin, neomycin, streptomycin, tobramycin, or a combination thereof. In an aspect, an aminoglycoside can comprise tobramycin.

In an aspect of a disclosed method, a container can be a glass container and can comprise a stopper or a seal. In an aspect, a container can be a non-glass container and can comprise a stopper or a seal. In an aspect, a stopper can comprise siliconized or non-siliconized rubber. In an aspect, rubber can be bromobutyl rubber or chlorobutyl rubber. In an aspect, a stopper or seal can comprise metal. In an aspect, a stopper or seal can comprise a Teflon coating or a Teflon treatment. In an aspect, a container can be a disposable packet. In an aspect, a disposable packet can be moisture-free. In an aspect, a container can be a glass or non-glass vial. In an aspect, a vial can be a 25 mL vial, a 50 mL vial, a 75 mL via, a 100 mL vial, a 125 mL vial, a 150 mL vial, a 175 mL vial, a 200 mL vial, a 250 mL vial, a 300 mL vial, a 350 mL vial, a 400 mL vial, a 450 mL vial, a 500 mL vial, or a 1000 mL vial. In an aspect, a vial can be range in size from about 25 mL to about 1000 mL. In an aspect, a vial can comprise a capsule or one or more capsules, each encapsulating a disclosed compounded composition.

In an aspect, a method of treating or preventing a fungal infection can comprise administering to the subject an oral pharmaceutical composition comprising one or more anti-infective agents. In an aspect, a method of treating or preventing a fungal infection can comprise administering to the subject an oral pharmaceutical composition comprising an anti-fungal agent. In an aspect, a method of treating or preventing a fungal infection method can comprise administering to the subject an oral pharmaceutical composition comprising an anti-bacterial agent (409).

In an aspect, a disclosed capsule can be added to water contained within a foot bath, wherein a capsule or in one or more capsules can disintegrate and the compounded composition can be dissolved in water contained within the foot bath. In an aspect, a disclosed capsule or one or more disclosed capsules can be opened or broken apart by a subject and the contents of the opened or broken capsule or one or more opened or broken capsules can be poured into water contained within a foot bath.

In an aspect, a disclosed method can be prophylactic, therapeutic, or both. As a prophylactic, a subject performs a disclosed method prior to onset (e.g., before developing a fungal infection) or during early onset (e.g., upon initial signs and symptoms of a fungal infection). In an aspect, as a prophylactic, a subject performs a disclosed method for a period of time prior to the manifestation of symptoms of a fungal infection. As a prophylactic, a disclosed method can be performed by a subject at risk of developing a fungal infection. As a therapeutic, a subject, for example, a subject diagnosed with a fungal infection, can perform a disclosed method so as to treat an active fungal infection.

In an aspect, a disclosed method can treat or prevent a fungal infection affecting the skin of at least a portion of a subject's foot or feet. In an aspect, a disclosed method can treat or prevent a fungal infection affecting the nail of at least one toe on a subject's foot or feet.

Figure 5:
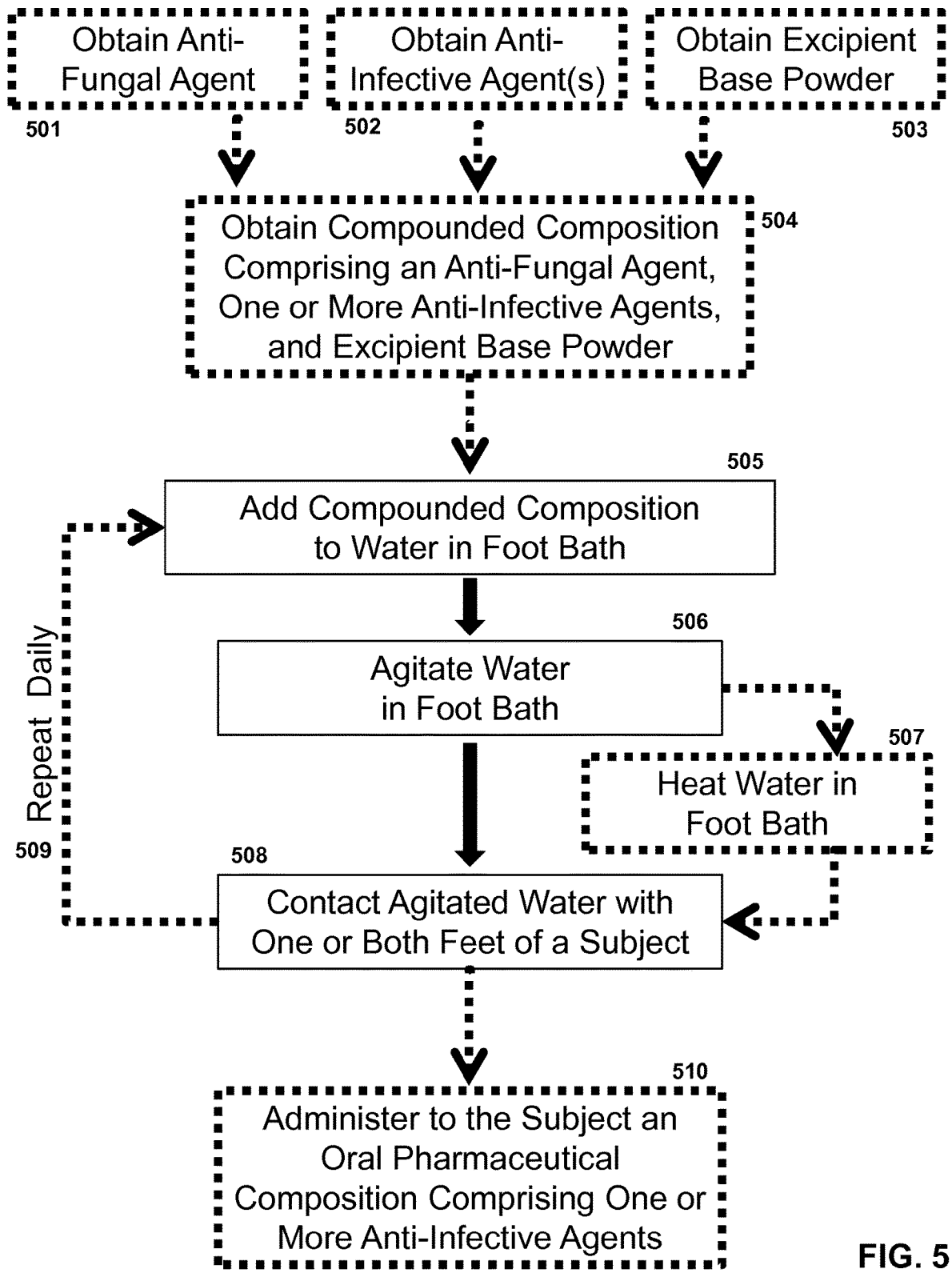
FIG. 5 shows a schematic of a disclosed method of treating or preventing of fungal infection in which the hatched boxes and lines represent steps of the method are optionally performed.

Disclosed herein is a method of treating or preventing a fungal infection, the method comprising: (i) adding to water contained within a foot bath a compounded composition comprising an anti-fungal agent, one or more additional anti-infective agents, and an excipient base powder comprising a blend a micronized xylitol and poloxamers (505); (ii) agitating the water contained within the foot bath (506); and (iii) contacting the agitated water with at least a portion of one or both feet of a subject (508). See FIG. 5, in which the hatched boxes and lines represent steps of the method are optionally performed.

In an aspect, a disclosed method can comprise obtaining a compounded composition (504). In an aspect, obtaining a compounded composition can comprise obtaining an anti-fungal agent (501), one or more anti-infective agents (502), an excipient base powder (503), or a combination thereof. In an aspect, obtaining an anti-fungal agent, one or more anti-infective agents, and an excipient base powder can comprise obtaining a bulk source of an anti-fungal agent, one or more anti-infective agents, or a combination thereof.

In an aspect, a compounded composition can be a dry powder formulation. In an aspect, a disclosed compounded composition can be encapsulated in a capsule or in one or more capsules.

In an aspect, a method of treating or preventing a fungal infection can comprise heating the water contained within the foot bath (507).

In an aspect of a disclosed method, a subject can be diagnosed with or can be suspected of having a fungal infection of at least a portion of one or both feet. In an aspect, a subject can have diabetes. In an aspect, a subject can be obese. In an aspect, a subject can have circulatory issues. In an aspect, a subject can be at risk of developing a fungal infection. For example, an at-risk subject can have damaged or moist skin, can have chronic disease, or can be immunocompromised.

In an aspect of a disclosed method, contacting the agitated water with at least a portion of one or both feet of a subject can comprise placing at least a portion of one or both feet of the subject in the foot bath (508). In an aspect, contacting the agitated water with at least a portion of one or both feet of a subject can comprise placing at least a portion of one or both feet of the subject in the foot bath for about 5 minutes to about 30 minutes. In an aspect, contacting the agitated water with at least a portion of one or both feet of a subject can comprise placing at least a portion of one or both feet of the subject in the foot bath for about 5 to about 20 minutes. In an aspect, contacting the agitated water with at least a portion of one or both feet of a subject can comprise placing at least a portion of one or both feet of the subject in the foot bath for about 10 minutes.

In an aspect of a disclosed method, an excipient base powder comprising a blend a micronized xylitol and poloxamers can be LoxaSperse™ excipient base powder. In an aspect, an excipient base powder comprising a blend a micronized xylitol and poloxamers can be XyliFos™ excipient base powder. In an aspect, XyliFos™ excipient base powder can comprise xylitol, poloxamer 407, hydroxylpropyl betadex, and epigallocatechin gallate. In an aspect, an excipient base powder can be obtained from a bulk source.

In an aspect of a disclosed method, an anti-fungal agent of a disclosed compounded composition can comprise abafungin, albaconazole, amorolfin, amphotericin b, anidulafungin, bifonazole, butenafine, butoconazole, candicidin, caspofungin, ciclopirox, clotrimazole, econazole, fenticonazole, filipin, fluconazole, flucytosine, griseofulvin, haloprogin, hamycin, isavuconazole, isoconazole, itraconazole, ketoconazole, micafungin, miconazole, naftifine, natamycin, nystatin, omoconazole, oxiconazole, polygodial, posaconazole, ravuconazole, rimocidin, sertaconazole, sulconazole, terbinafine, terconazole, tioconazole, tolnaftate, undecylenic acid, voriconazole, or a combination thereof. In an aspect, an anti-fungal agent can comprise fluconazole, itraconazole, voriconazole, or a combination thereof. In an aspect, an anti-fungal agent can comprise fluconazole. In an aspect, an anti-fungal agent can comprise itraconazole or voriconazole or a combination thereof. In an aspect, an anti-fungal agent can comprise a dry powder and can be obtained from a bulk source.

In an aspect, the ratio of an anti-fungal agent to excipient base powder in a disclosed compounded composition can be from about 1:60 to about 1:3. In an aspect, the ratio of an anti-fungal agent to excipient base powder in a disclosed compounded composition can be from about 1:60 to about 1:6. In an aspect, the ratio of an anti-fungal agent to excipient base powder in a disclosed compounded composition can be from about 1:30 to about 1:3. In an aspect, the ratio of an anti-fungal agent to excipient base powder in a disclosed compounded composition can be from about 1:20 to about 1:2. In an aspect, the ratio of an anti-fungal agent to excipient base powder in a disclosed compounded composition can be about 1:15. In an aspect, the amount of fluconazole in a disclosed compounded composition can be from about 200 mg to about 1000 mg and the amount of excipient base powder can be about 3 g. In an aspect, the amount of fluconazole in a disclosed compounded composition can be about 200 mg and the amount of excipient base powder can be about 3 g. In an aspect, the amount of fluconazole in a disclosed compounded composition can be about 1000 mg and the amount of excipient base powder can be about 3 g. In an aspect, the amount of itraconazole or voriconazole or a combination thereof in a disclosed compounded composition can be from about 50 mg to about 500 mg and the amount of excipient base powder can be about 3 g. In an aspect, the amount of itraconazole or voriconazole or a combination thereof in a disclosed compounded composition can be from about 200 mg and the amount of excipient base powder can be about 3 g.

In an aspect, a method of treating or preventing a fungal infection can comprise repeating steps (i)-(iii) daily (509). In an aspect, a method of treating or preventing a fungal infection can comprise repeating steps (i)-(iii) daily until the fungal infection or suspected fungal infection is eradicated.

In an aspect of a disclosed method, an additional anti-infective agent can comprise an anti-fungal agent, an anti-bacterial agent, or a combination thereof. In an aspect, an anti-infective agent can comprise a dry powder and can be obtained from a bulk source. In an aspect, the ratio of an additional anti-infective agent to excipient base powder in a disclosed compounded composition can be from about 1:60 to about 1:3. In an aspect, the ratio of an additional anti-infective agent to excipient base powder in a disclosed compounded composition can be from about 1:60 to about 1:6. In an aspect, the ratio of an additional anti-infective agent to excipient base powder in a disclosed compounded composition can be from about 1:30 to about 1:3. In an aspect, the ratio of an additional anti-infective agent to excipient base powder can be from about 1:20 to about 1:2. In an aspect, the ratio of additional anti-infective agent to excipient base powder can be about 1:15.

In an aspect of a disclosed method, an anti-bacterial agent can comprise afenide, amikacin, amoxicillin, ampicillin, arsphenamine, azithromycin, azlocillin, aztreonam, bacampicillin, bacitracin, carbacephem (loracarbef), carbenicillin, cefaclor, cefadroxil, cefalotin, cefamandole, cefazolin, cefdinir, cefditoren, cefepime, cefixime, cefoperazone, cefotaxime, cefoxitin, cefpodoxime, cefprozil, ceftazidime, ceftibuten, ceftizoxime, ceftobiprole, ceftriaxone, cefuroxime, cephalexin, chloramphenicol, chlorhexidine, ciprofloxacin, clarithromycin, clavulanic acid, clindamycin, cloxacillin, colimycin, colistimethate teicoplanin, colistin, demeclocycline, dicloxacillin, dirithromycin, doripenem, doxycycline, efprozil, enoxacin, ertapenem, erythromycin, ethambutol, flucloxacillin, fosfomycin, furazolidone, gatifloxacin, geldanamycin, gemifloxacin, gentamicin, grepafloxacin, herbimycin, imipenem, isoniazid, kanamycin, levofloxacin, lincomycin, linezolid, lomefloxacin, meropenem, meticillin, metronidazole, mezlocillin, minocycline, mitomycin, moxifloxacin, mupirocin, nafcillin, neomycin, netilmicin, nitrofurantoin, norfloxacin, ofloxacin, oxacillin, oxytetracycline, paromomycin, penicillin G, penicillin V, piperacillin, pivmecillinam, platensimycin, polymyxin B, prontosil, pvampicillin, pyrazinamide, quinupristin/dalfopristin, rifampicin, rifampin, roxithromycin, sparfloxacin, spectinomycin, spiramycin, sulbactam, sulfacetamide, sulfamethizole, sulfamethoxazole, sulfanilimide, sulfisoxazole, sulphonamides, sultamicillin, telithromycin, tetracycline, thiamphenicol, ticarcillin, tobramycin, trimethoprim, trimethoprim-sulfamethoxazole, troleandomycin, trovafloxacin, or a combination thereof. In an aspect, an anti-bacterial agent can comprise a quinolone. In an aspect, a quinolone can comprise ciprofloxacin, enoxacin, gatifloxacin, gemifloxacin, grepafloxacin, levofloxacin, lomefloxacin, moxifloxacin, nalidixic acid, norfloxacin, ofloxacin, sparfloxacin, trovafloxacin, or a combination thereof. In an aspect, a quinolone can comprise levofloxacin. In an aspect, an anti-bacterial agent can comprise an aminoglycoside. In an aspect, an aminoglycoside can comprise amikacin, gentamicin, kanamycin, neomycin, streptomycin, tobramycin, or a combination thereof. In an aspect, an aminoglycoside can comprise tobramycin.

In an aspect of a disclosed method, a container can be a glass container and can comprise a stopper or a seal. In an aspect, a container can be a non-glass container and can comprise a stopper or a seal. In an aspect, a stopper can comprise siliconized or non-siliconized rubber. In an aspect, rubber can be bromobutyl rubber or chlorobutyl rubber. In an aspect, a stopper or seal can comprise metal. In an aspect, a stopper or seal can comprise a Teflon coating or a Teflon treatment. In an aspect, a container can be a disposable packet. In an aspect, a disposable packet can be moisture-free. In an aspect, a container can be a glass or non-glass vial. In an aspect, a vial can be a 25 mL vial, a 50 mL vial, a 75 mL via, a 100 mL vial, a 125 mL vial, a 150 mL vial, a 175 mL vial, a 200 mL vial, a 250 mL vial, a 300 mL vial, a 350 mL vial, a 400 mL vial, a 450 mL vial, a 500 mL vial, or a 1000 mL vial. In an aspect, a vial can be range in size from about 25 mL to about 1000 mL. In an aspect, a vial can comprise a capsule or one or more capsules, each encapsulating a disclosed compounded composition.

In an aspect, a method of treating or preventing a fungal infection can comprise administering to the subject an oral pharmaceutical composition comprising one or more anti-infective agents (510). In an aspect, a method of treating or preventing a fungal infection can comprise administering to the subject an oral pharmaceutical composition comprising an anti-fungal agent. In an aspect, a method of treating or preventing a fungal infection method can comprise administering to the subject an oral pharmaceutical composition comprising an anti-bacterial agent.

In an aspect, a disclosed capsule can be added to water contained within a foot bath, wherein a capsule or in one or more capsules can disintegrate and the compounded composition can be dissolved in water contained within the foot bath. In an aspect, a disclosed capsule or one or more disclosed capsules can be opened or broken apart by a subject and the contents of the opened or broken capsule or one or more opened or broken capsules can be poured into water contained within a foot bath.

In an aspect, a disclosed method can be prophylactic, therapeutic, or both. As a prophylactic, a subject performs a disclosed method prior to onset (e.g., before developing a fungal infection) or during early onset (e.g., upon initial signs and symptoms of a fungal infection). In an aspect, as a prophylactic, a subject performs a disclosed method for a period of time prior to the manifestation of symptoms of a fungal infection. As a prophylactic, a disclosed method can be performed by a subject at risk of developing a fungal infection. As a therapeutic, a subject, for example, a subject diagnosed with a fungal infection, can perform a disclosed method so as to treat an active fungal infection.

In an aspect, a disclosed method can treat or prevent a fungal infection affecting the skin of at least a portion of a subject's foot or feet. In an aspect, a disclosed method can treat or prevent a fungal infection affecting the nail of at least one toe on a subject's foot or feet.

2. Methods of Making a Compounded Composition

Disclosed herein is a method of making a compounded composition for treating or preventing a fungal infection using a foot bath, the method comprising: obtaining an anti-fungal agent, an excipient base powder comprising a blend of micronized xylitol and poloxamers, or both; mixing a therapeutically effective amount of the anti-fungal agent and a sufficient amount of the excipient base powder to make a homogenous compounded composition.

Disclosed herein is a method of making any compounded composition disclosed herein.

Disclosed herein is a method of making a compounded composition, the method comprising: mixing a therapeutically effective amount of an anti-fungal agent and a sufficient amount of an excipient base powder comprising a blend of micronized xylitol and poloxamers to make a compounded composition (103). See FIG. 1, in which the hatched boxes and lines represent steps of the method are optionally performed. In an aspect, a compounded composition can be a dry powder formulation. In an aspect, a compounded composition can be a homogenous dry powder formulation. In an aspect, a disclosed compounded composition can be encapsulated in a or one or more capsules or one or more capsules (104).

In an aspect of a disclosed method, a method of making a compounded composition can comprise obtaining an anti-fungal agent (101), an excipient base powder (102), or both. In an aspect, obtaining an anti-fungal agent, obtaining an excipient base powder, or both can comprise obtaining a bulk source of an anti-fungal agent, an excipient base powder, or both.

In an aspect of a disclosed method, an excipient base powder comprising a blend a micronized xylitol and poloxamers can be LoxaSperse™ excipient base powder. In an aspect, an excipient base powder comprising a blend a micronized xylitol and poloxamers can be XyliFos™ excipient base powder. In an aspect, XyliFos™ excipient base powder can comprise xylitol, poloxamer 407, hydroxylpropyl betadex, and epigallocatechin gallate. In an aspect, an excipient base powder can be obtained from a bulk source.

In an aspect of a disclosed method, an anti-fungal agent can comprise abafungin, albaconazole, amorolfin, amphotericin b, anidulafungin, bifonazole, butenafine, butoconazole, candicidin, caspofungin, ciclopirox, clotrimazole, econazole, fenticonazole, filipin, fluconazole, flucytosine, griseofulvin, haloprogin, hamycin, isavuconazole, isoconazole, itraconazole, ketoconazole, micafungin, miconazole, naftifine, natamycin, nystatin, omoconazole, oxiconazole, polygodial, posaconazole, ravuconazole, rimocidin, sertaconazole, sulconazole, terbinafine, terconazole, tioconazole, tolnaftate, undecylenic acid, voriconazole, or a combination thereof. In an aspect, an anti-fungal agent can comprise fluconazole, itraconazole, voriconazole, or a combination thereof. In an aspect, an anti-fungal agent can comprise fluconazole. In an aspect, an anti-fungal agent can comprise itraconazole or voriconazole or a combination thereof.

In an aspect, the ratio of an anti-fungal agent to excipient base powder in a disclosed compounded composition can be from about 1:60 to about 1:3. In an aspect, the ratio of an anti-fungal agent to excipient base powder in a disclosed compounded composition can be from about 1:60 to about 1:6. In an aspect, the ratio of an anti-fungal agent to excipient base powder in a disclosed compounded composition can be from about 1:30 to about 1:3. In an aspect, the ratio of an anti-fungal agent to excipient base powder in a disclosed compounded composition can be from about 1:20 to about 1:2. In an aspect, the ratio of an anti-fungal agent to excipient base powder in a disclosed compounded composition can be about 1:15. In an aspect, the amount of fluconazole in a disclosed compounded composition can be from about 200 mg to about 1000 mg and the amount of excipient base powder can be about 3 g. In an aspect, the amount of fluconazole in a disclosed compounded composition can be about 200 mg and the amount of excipient base powder can be about 3 g. In an aspect, the amount of fluconazole in a disclosed compounded composition can be about 1000 mg and the amount of excipient base powder can be about 3 g. In an aspect, the amount of itraconazole or voriconazole or a combination thereof in a disclosed compounded composition can be from about 50 mg to about 500 mg and the amount of excipient base powder can be about 3 g. In an aspect, the amount of itraconazole or voriconazole or a combination thereof in a disclosed compounded composition can be from about 200 mg and the amount of excipient base powder can be about 3 g.

In an aspect, a method of making a compounded composition can comprise mixing a therapeutically effective amount of one or more additional anti-infective agents with the anti-fungal agent and the excipient base powder.

For example, in an aspect of a disclosed method, a disclosed compounded composition can comprise one or more additional anti-infective agents. In an aspect, an additional anti-infective agent can comprise an anti-fungal agent, an anti-bacterial agent, or a combination thereof. In an aspect, an anti-infective agent can comprise a dry powder and can be obtained from a bulk source. In an aspect, the ratio of an additional anti-infective agent to excipient base powder in a disclosed compounded composition can be from about 1:60 to about 1:3. In an aspect, the ratio of an additional anti-infective agent to excipient base powder in a disclosed compounded composition can be from about 1:60 to about 1:6. In an aspect, the ratio of an additional anti-infective agent to excipient base powder in a disclosed compounded composition can be from about 1:30 to about 1:3. In an aspect, the ratio of an additional anti-infective agent to excipient base powder can be from about 1:20 to about 1:2. In an aspect, the ratio of additional anti-infective agent to excipient base powder can be about 1:15.

In an aspect of a disclosed method, an anti-bacterial agent can comprise afenide, amikacin, amoxicillin, ampicillin, arsphenamine, azithromycin, azlocillin, aztreonam, bacampicillin, bacitracin, carbacephem (loracarbef), carbenicillin, cefaclor, cefadroxil, cefalotin, cefamandole, cefazolin, cefdinir, cefditoren, cefepime, cefixime, cefoperazone, cefotaxime, cefoxitin, cefpodoxime, cefprozil, ceftazidime, ceftibuten, ceftizoxime, ceftobiprole, ceftriaxone, cefuroxime, cephalexin, chloramphenicol, chlorhexidine, ciprofloxacin, clarithromycin, clavulanic acid, clindamycin, cloxacillin, colimycin, colistimethate teicoplanin, colistin, demeclocycline, dicloxacillin, dirithromycin, doripenem, doxycycline, efprozil, enoxacin, ertapenem, erythromycin, ethambutol, flucloxacillin, fosfomycin, furazolidone, gatifloxacin, geldanamycin, gemifloxacin, gentamicin, grepafloxacin, herbimycin, imipenem, isoniazid, kanamycin, levofloxacin, lincomycin, linezolid, lomefloxacin, meropenem, meticillin, metronidazole, mezlocillin, minocycline, mitomycin, moxifloxacin, mupirocin, nafcillin, neomycin, netilmicin, nitrofurantoin, norfloxacin, ofloxacin, oxacillin, oxytetracycline, paromomycin, penicillin G, penicillin V, piperacillin, pivmecillinam, platensimycin, polymyxin B, prontosil, pvampicillin, pyrazinamide, quinupristin/dalfopristin, rifampicin, rifampin, roxithromycin, sparfloxacin, spectinomycin, spiramycin, sulbactam, sulfacetamide, sulfamethizole, sulfamethoxazole, sulfanilimide, sulfisoxazole, sulphonamides, sultamicillin, telithromycin, tetracycline, thiamphenicol, ticarcillin, tobramycin, trimethoprim, trimethoprim-sulfamethoxazole, troleandomycin, trovafloxacin, or a combination thereof. In an aspect, an anti-bacterial agent can comprise a quinolone. In an aspect, a quinolone can comprise ciprofloxacin, enoxacin, gatifloxacin, gemifloxacin, grepafloxacin, levofloxacin, lomefloxacin, moxifloxacin, nalidixic acid, norfloxacin, ofloxacin, sparfloxacin, trovafloxacin, or a combination thereof. In an aspect, a quinolone can comprise levofloxacin. In an aspect, an anti-bacterial agent can comprise an aminoglycoside. In an aspect, an aminoglycoside can comprise amikacin, gentamicin, kanamycin, neomycin, streptomycin, tobramycin, or a combination thereof. In an aspect, an aminoglycoside can comprise tobramycin.

In an aspect, a method of making a compounded composition can comprise packaging the compounded composition into a container and sealing the container (105).

In an aspect of a disclosed method, a container can be a glass container and can comprise a stopper or a seal. In an aspect, a container can be a non-glass container and can comprise a stopper or a seal. In an aspect, a stopper can comprise siliconized or non-siliconized rubber. In an aspect, rubber can be bromobutyl rubber or chlorobutyl rubber. In an aspect, a stopper or seal can comprise metal. In an aspect, a stopper or seal can comprise a Teflon coating or a Teflon treatment. In an aspect, a container can be a disposable packet. In an aspect, a disposable packet can be moisture-free. In an aspect, a container can be a glass or non-glass vial. In an aspect, a vial can be a 25 mL vial, a 50 mL vial, a 75 mL via, a 100 mL vial, a 125 mL vial, a 150 mL vial, a 175 mL vial, a 200 mL vial, a 250 mL vial, a 300 mL vial, a 350 mL vial, a 400 mL vial, a 450 mL vial, a 500 mL vial, or a 1000 mL vial. In an aspect, a vial can be range in size from about 25 mL to about 1000 mL. In an aspect, a vial can comprise a capsule or one or more capsule encapsulating a disclosed compounded composition.

In an aspect, a method of making a compounded composition can comprise obtaining an additional anti-infective agent. In an aspect, obtaining an additional anti-infective agent can comprise obtaining a bulk source of an anti-infective agent.

In an aspect, a method of making a compounded composition can comprise encapsulating a compounded composition (104).

In an aspect, a method can comprise sterilizing a compounded composition (106).

Figure 2:
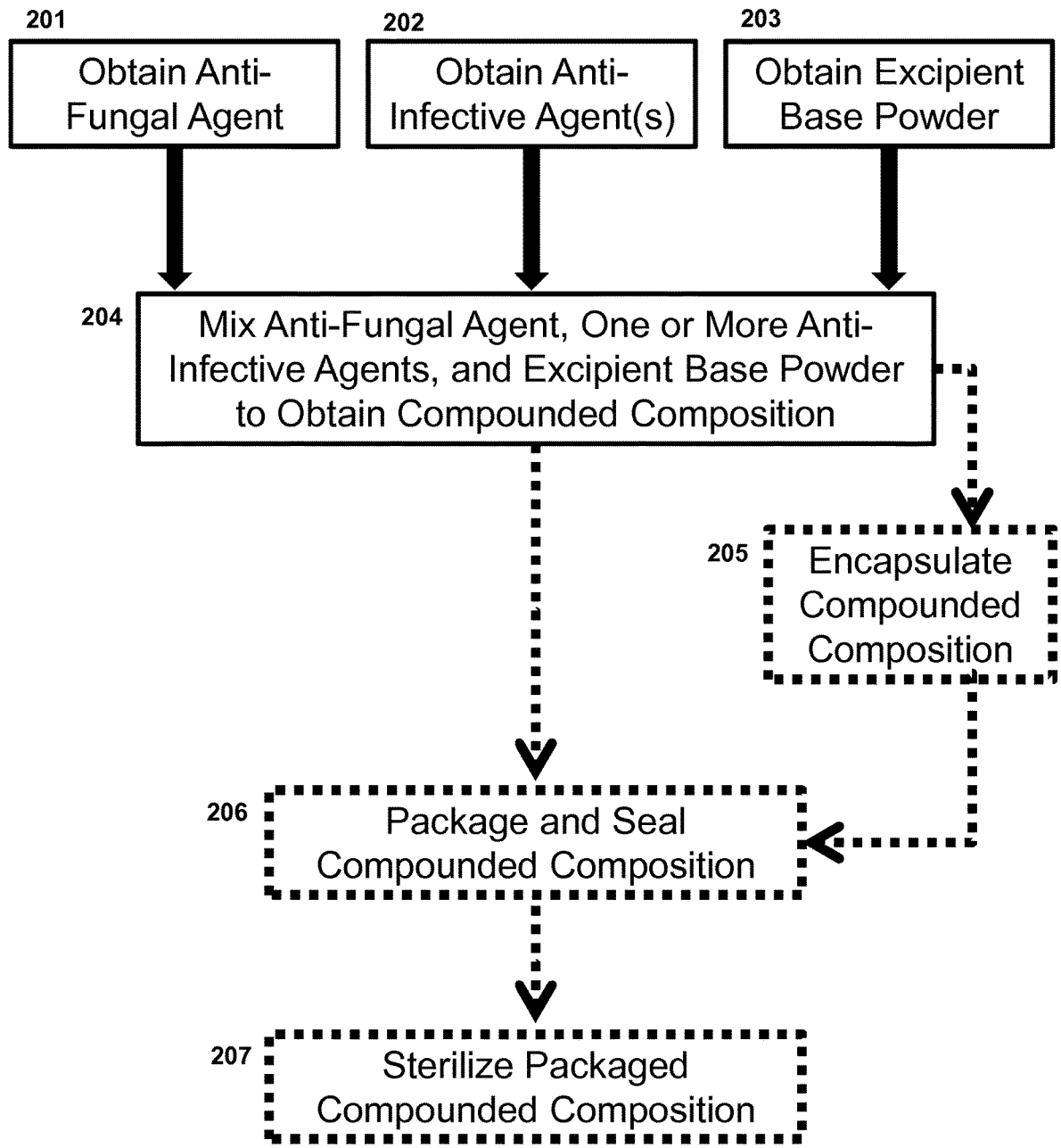
FIG. 2 shows a schematic of a disclosed method of making a compounded composition, wherein the compounded composition comprises an anti-fungal agent, one or more anti-infective agents, and an excipient base powder.

Disclosed herein is a method of making a compounded composition, the method comprising: mixing a therapeutically effective amount of an anti-fungal agent, a therapeutically effective amount of one or more additional anti-infective agents, and a sufficient amount of an excipient base powder comprising a blend of micronized xylitol and poloxamers to make a compounded composition (204). See FIG. 2, in which the hatched boxes and lines represent steps of the method are optionally performed.

In an aspect, a compounded composition can be a dry powder formulation. In an aspect, a compounded composition can be a homogenous dry powder formulation. In an aspect, a disclosed compounded composition can be encapsulated in a capsule or in one or more capsules.

In an aspect, a method of making a compounded composition can comprise obtaining an anti-fungal agent (201), one or more anti-infective agents (202), an excipient base powder (203), or a combination thereof.

In an aspect, obtaining an anti-fungal agent, obtaining one or more anti-infective agents, obtaining an excipient base powder, or a combination thereof can comprise obtaining a bulk source of an anti-fungal agent, one or more anti-infective agents, an excipient base powder, or a combination thereof.

In an aspect, an excipient base powder comprising a blend a micronized xylitol and poloxamers can be LoxaSperse™ excipient base powder. In an aspect, an excipient base powder comprising a blend a micronized xylitol and poloxamers can be XyliFos™ excipient base powder. In an aspect, XyliFos™ excipient base powder can comprise xylitol, poloxamer 407, hydroxylpropyl betadex, and epigallocatechin gallate. In an aspect, an excipient base powder can be obtained from a bulk source.

In an aspect, an anti-fungal agent can comprise abafungin, albaconazole, amorolfin, amphotericin b, anidulafungin, bifonazole, butenafine, butoconazole, candicidin, caspofungin, ciclopirox, clotrimazole, econazole, fenticonazole, filipin, fluconazole, flucytosine, griseofulvin, haloprogin, hamycin, isavuconazole, isoconazole, itraconazole, ketoconazole, micafungin, miconazole, naftifine, natamycin, nystatin, omoconazole, oxiconazole, polygodial, posaconazole, ravuconazole, rimocidin, sertaconazole, sulconazole, terbinafine, terconazole, tioconazole, tolnaftate, undecylenic acid, voriconazole, or a combination thereof. In an aspect, an anti-fungal agent can comprise fluconazole, itraconazole, voriconazole, or a combination thereof. In an aspect, an anti-fungal agent can comprise fluconazole. In an aspect, an anti-fungal agent can comprise itraconazole or voriconazole or a combination thereof.

In an aspect, the ratio of an anti-fungal agent to excipient base powder in a disclosed compounded composition can be from about 1:60 to about 1:3. In an aspect, the ratio of an anti-fungal agent to excipient base powder in a disclosed compounded composition can be from about 1:60 to about 1:6. In an aspect, the ratio of an anti-fungal agent to excipient base powder in a disclosed compounded composition can be from about 1:30 to about 1:3. In an aspect, the ratio of an anti-fungal agent to excipient base powder in a disclosed compounded composition can be from about 1:20 to about 1:2. In an aspect, the ratio of an anti-fungal agent to excipient base powder in a disclosed compounded composition can be about 1:15. In an aspect, the amount of fluconazole in a disclosed compounded composition can be from about 200 mg to about 1000 mg and the amount of excipient base powder can be about 3 g. In an aspect, the amount of fluconazole in a disclosed compounded composition can be about 200 mg and the amount of excipient base powder can be about 3 g. In an aspect, the amount of fluconazole in a disclosed compounded composition can be about 1000 mg and the amount of excipient base powder can be about 3 g. In an aspect, the amount of itraconazole or voriconazole or a combination thereof in a disclosed compounded composition can be from about 50 mg to about 500 mg and the amount of excipient base powder can be about 3 g. In an aspect, the amount of itraconazole or voriconazole or a combination thereof in a disclosed compounded composition can be from about 200 mg and the amount of excipient base powder can be about 3 g.

In an aspect, an additional anti-infective agent can comprise an anti-fungal agent, an anti-bacterial agent, or a combination thereof. In an aspect, an anti-infective agent can comprise a dry powder and can be obtained from a bulk source. In an aspect, the ratio of an additional anti-infective agent to excipient base powder in a disclosed compounded composition can be from about 1:60 to about 1:3. In an aspect, the ratio of an additional anti-infective agent to excipient base powder in a disclosed compounded composition can be from about 1:60 to about 1:6. In an aspect, the ratio of an additional anti-infective agent to excipient base powder in a disclosed compounded composition can be from about 1:30 to about 1:3. In an aspect, the ratio of an additional anti-infective agent to excipient base powder can be from about 1:20 to about 1:2. In an aspect, the ratio of additional anti-infective agent to excipient base powder can be about 1:15.

In an aspect, an anti-bacterial agent can comprise afenide, amikacin, amoxicillin, ampicillin, arsphenamine, azithromycin, azlocillin, aztreonam, bacampicillin, bacitracin, carbacephem (loracarbef), carbenicillin, cefaclor, cefadroxil, cefalotin, cefamandole, cefazolin, cefdinir, cefditoren, cefepime, cefixime, cefoperazone, cefotaxime, cefoxitin, cefpodoxime, cefprozil, ceftazidime, ceftibuten, ceftizoxime, ceftobiprole, ceftriaxone, cefuroxime, cephalexin, chloramphenicol, chlorhexidine, ciprofloxacin, clarithromycin, clavulanic acid, clindamycin, cloxacillin, colimycin, colistimethate teicoplanin, colistin, demeclocycline, dicloxacillin, dirithromycin, doripenem, doxycycline, efprozil, enoxacin, ertapenem, erythromycin, ethambutol, flucloxacillin, fosfomycin, furazolidone, gatifloxacin, gemifloxacin, geldanamycin, gemifloxacin, gentamicin, grepafloxacin, herbimycin, imipenem, isoniazid, kanamycin, levofloxacin, lincomycin, linezolid, lomefloxacin, meropenem, meticillin, metronidazole, mezlocillin, minocycline, mitomycin, moxifloxacin, mupirocin, nafcillin, neomycin, netilmicin, nitrofurantoin, norfloxacin, ofloxacin, oxacillin, oxytetracycline, paromomycin, penicillin G, penicillin V, piperacillin, pivmecillinam, platensimycin, polymyxin B, prontosil, pvampicillin, pyrazinamide, quinupristin/dalfopristin, rifampicin, rifampin, roxithromycin, sparfloxacin, spectinomycin, spiramycin, sulbactam, sulfacetamide, sulfamethizole, sulfamethoxazole, sulfanilimide, sulfisoxazole, sulphonamides, sultamicillin, telithromycin, tetracycline, thiamphenicol, ticarcillin, tobramycin, trimethoprim, trimethoprim-sulfamethoxazole, troleandomycin, trovafloxacin, or a combination thereof. In an aspect, an anti-bacterial agent can comprise a quinolone. In an aspect, a quinolone can comprise ciprofloxacin, enoxacin, gatifloxacin, gemifloxacin, grepafloxacin, levofloxacin, lomefloxacin, moxifloxacin, nalidixic acid, norfloxacin, ofloxacin, sparfloxacin, trovafloxacin, or a combination thereof. In an aspect, a quinolone can comprise levofloxacin. In an aspect, an anti-bacterial agent can comprise an aminoglycoside. In an aspect, an aminoglycoside can comprise amikacin, gentamicin, kanamycin, neomycin, streptomycin, tobramycin, or a combination thereof. In an aspect, an aminoglycoside can comprise tobramycin.

In an aspect, a method of making a compounded composition can comprise packaging the compounded composition into a container and sealing the container (206).

In an aspect, a container can be a glass container and can comprise a stopper or a seal. In an aspect, a container can be a non-glass container and can comprise a stopper or a seal. In an aspect, a stopper can comprise siliconized or non-siliconized rubber. In an aspect, rubber can be bromobutyl rubber or chlorobutyl rubber. In an aspect, a stopper or seal can comprise metal. In an aspect, a stopper or seal can comprise a Teflon coating or a Teflon treatment. In an aspect, a container can be a disposable packet. In an aspect, a disposable packet can be moisture-free. In an aspect, a container can be a glass or non-glass vial. In an aspect, a vial can be a 25 mL vial, a 50 mL vial, a 75 mL via, a 100 mL vial, a 125 mL vial, a 150 mL vial, a 175 mL vial, a 200 mL vial, a 250 mL vial, a 300 mL vial, a 350 mL vial, a 400 mL vial, a 450 mL vial, a 500 mL vial, or a 1000 mL vial. In an aspect, a vial can be range in size from about 25 mL to about 1000 mL. In an aspect, a vial can comprise a capsule or one or more capsules, each encapsulating a disclosed compounded composition.

In an aspect, a disclosed method can comprise encapsulating a compounded composition (205). In an aspect, a disclosed method can comprise sterilizing a compounded composition (207).

Disclosed herein is a method of making a compounded composition, the method comprising: mixing a therapeutically effective amount of an anti-fungal agent, a therapeutically effective amount of one or more additional anti-infective agents, and a sufficient amount of an excipient base powder comprising a blend of micronized xylitol and poloxamers to make a compounded composition.

In an aspect of a disclosed method, a compounded composition can be a dry powder formulation. In an aspect, a compounded composition can be a homogenous dry powder formulation. In an aspect, a disclosed compounded composition can be encapsulated in a capsule or in one or more capsules.

In an aspect, a method of making a compounded composition can comprise obtaining an anti-fungal agent, one or more anti-infective agents, an excipient base powder, or a combination thereof.

In an aspect of a disclosed method, obtaining an anti-fungal agent, obtaining one or more anti-infective agents, obtaining an excipient base powder, or a combination thereof can comprise obtaining a bulk source of an anti-fungal agent, one or more anti-infective agents, an excipient base powder, or a combination thereof.

In an aspect of a disclosed method, an excipient base powder comprising a blend a micronized xylitol and poloxamers can be LoxaSperse™ excipient base powder. In an aspect, an excipient base powder comprising a blend a micronized xylitol and poloxamers can be XyliFos™ excipient base powder. In an aspect, XyliFos™ excipient base powder can comprise xylitol, poloxamer 407, hydroxylpropyl betadex, and epigallocatechin gallate. In an aspect, an excipient base powder can be obtained from a bulk source.

In an aspect of a disclosed method, an anti-fungal agent can comprise abafungin, albaconazole, amorolfin, amphotericin b, anidulafungin, bifonazole, butenafine, butoconazole, candicidin, caspofungin, ciclopirox, clotrimazole, econazole, fenticonazole, filipin, fluconazole, flucytosine, griseofulvin, haloprogin, hamycin, isavuconazole, isoconazole, itraconazole, ketoconazole, micafungin, miconazole, naftifine, natamycin, nystatin, omoconazole, oxiconazole, polygodial, posaconazole, ravuconazole, rimocidin, sertaconazole, sulconazole, terbinafine, terconazole, tioconazole, tolnaftate, undecylenic acid, voriconazole, or a combination thereof. In an aspect, an anti-fungal agent can comprise fluconazole, itraconazole, voriconazole, or a combination thereof. In an aspect, an anti-fungal agent can comprise fluconazole. In an aspect, an anti-fungal agent can comprise itraconazole or voriconazole or a combination thereof.

In an aspect, the ratio of an anti-fungal agent to excipient base powder in a disclosed compounded composition can be from about 1:60 to about 1:3. In an aspect, the ratio of an anti-fungal agent to excipient base powder in a disclosed compounded composition can be from about 1:60 to about 1:6. In an aspect, the ratio of an anti-fungal agent to excipient base powder in a disclosed compounded composition can be from about 1:30 to about 1:3. In an aspect, the ratio of an anti-fungal agent to excipient base powder in a disclosed compounded composition can be from about 1:20 to about 1:2. In an aspect, the ratio of an anti-fungal agent to excipient base powder in a disclosed compounded composition can be about 1:15. In an aspect, the amount of fluconazole in a disclosed compounded composition can be from about 200 mg to about 1000 mg and the amount of excipient base powder can be about 3 g. In an aspect, the amount of fluconazole in a disclosed compounded composition can be about 200 mg and the amount of excipient base powder can be about 3 g. In an aspect, the amount of fluconazole in a disclosed compounded composition can be about 1000 mg and the amount of excipient base powder can be about 3 g. In an aspect, the amount of itraconazole or voriconazole or a combination thereof in a disclosed compounded composition can be from about 50 mg to about 500 mg and the amount of excipient base powder can be about 3 g. In an aspect, the amount of itraconazole or voriconazole or a combination thereof in a disclosed compounded composition can be from about 200 mg and the amount of excipient base powder can be about 3 g.

In an aspect of a disclosed method, an additional anti-infective agent can comprise an anti-fungal agent, an anti-bacterial agent, or a combination thereof. In an aspect, an anti-infective agent can comprise a dry powder and can be obtained from a bulk source. In an aspect, the ratio of an additional anti-infective agent to excipient base powder in a disclosed compounded composition can be from about 1:60 to about 1:3. In an aspect, the ratio of an additional anti-infective agent to excipient base powder in a disclosed compounded composition can be from about 1:60 to about 1:6. In an aspect, the ratio of an additional anti-infective agent to excipient base powder in a disclosed compounded composition can be from about 1:30 to about 1:3. In an aspect, the ratio of an additional anti-infective agent to excipient base powder can be from about 1:20 to about 1:2. In an aspect, the ratio of additional anti-infective agent to excipient base powder can be about 1:15.

In an aspect of a disclosed method, an anti-bacterial agent can comprise afenide, amikacin, amoxicillin, ampicillin, arsphenamine, azithromycin, azlocillin, aztreonam, bacampicillin, bacitracin, carbacephem (loracarbef), carbenicillin, cefaclor, cefadroxil, cefalotin, cefamandole, cefazolin, cefdinir, cefditoren, cefepime, cefixime, cefoperazone, cefotaxime, cefoxitin, cefpodoxime, cefprozil, ceftazidime, ceftibuten, ceftizoxime, ceftobiprole, ceftriaxone, cefuroxime, cephalexin, chloramphenicol, chlorhexidine, ciprofloxacin, clarithromycin, clavulanic acid, clindamycin, cloxacillin, colimycin, colistimethate teicoplanin, colistin, demeclocycline, dicloxacillin, dirithromycin, doripenem, doxycycline, efprozil, enoxacin, ertapenem, erythromycin, ethambutol, flucloxacillin, fosfomycin, furazolidone, gatifloxacin, geldanamycin, gemifloxacin, gentamicin, grepafloxacin, herbimycin, imipenem, isoniazid, kanamycin, levofloxacin, lincomycin, linezolid, lomefloxacin, meropenem, meticillin, metronidazole, mezlocillin, minocycline, mitomycin, moxifloxacin, mupirocin, nafcillin, neomycin, netilmicin, nitrofurantoin, norfloxacin, ofloxacin, oxacillin, oxytetracycline, paromomycin, penicillin G, penicillin V, piperacillin, pivmecillinam, platensimycin, polymyxin B, prontosil, pvampicillin, pyrazinamide, quinupristin/dalfopristin, rifampicin, rifampin, roxithromycin, sparfloxacin, spectinomycin, spiramycin, sulbactam, sulfacetamide, sulfamethizole, sulfamethoxazole, sulfanilimide, sulfisoxazole, sulphonamides, sultamicillin, telithromycin, tetracycline, thiamphenicol, ticarcillin, tobramycin, trimethoprim, trimethoprim-sulfamethoxazole, troleandomycin, trovafloxacin, or a combination thereof. In an aspect, an anti-bacterial agent can comprise a quinolone. In an aspect, a quinolone can comprise ciprofloxacin, enoxacin, gatifloxacin, gemifloxacin, grepafloxacin, levofloxacin, lomefloxacin, moxifloxacin, nalidixic acid, norfloxacin, ofloxacin, sparfloxacin, trovafloxacin, or a combination thereof. In an aspect, a quinolone can comprise levofloxacin. In an aspect, an anti-bacterial agent can comprise an aminoglycoside. In an aspect, an aminoglycoside can comprise amikacin, gentamicin, kanamycin, neomycin, streptomycin, tobramycin, or a combination thereof. In an aspect, an aminoglycoside can comprise tobramycin.

In an aspect, a disclosed method of making a compounded composition can comprise packaging the compounded composition into a container and sealing the container.

In an aspect of a disclosed method, a container can be a glass container and can comprise a stopper or a seal. In an aspect, a container can be a non-glass container and can comprise a stopper or a seal. In an aspect, a stopper can comprise siliconized or non-siliconized rubber. In an aspect, rubber can be bromobutyl rubber or chlorobutyl rubber. In an aspect, a stopper or seal can comprise metal. In an aspect, a stopper or seal can comprise a Teflon coating or a Teflon treatment. In an aspect, a container can be a disposable packet. In an aspect, a disposable packet can be moisture-free. In an aspect, a container can be a glass or non-glass vial. In an aspect, a vial can be a 25 mL vial, a 50 mL vial, a 75 mL via, a 100 mL vial, a 125 mL vial, a 150 mL vial, a 175 mL vial, a 200 mL vial, a 250 mL vial, a 300 mL vial, a 350 mL vial, a 400 mL vial, a 450 mL vial, a 500 mL vial, or a 1000 mL vial. In an aspect, a vial can be range in size from about 25 mL to about 1000 mL. In an aspect, a vial can comprise a capsule or one or more capsules, each encapsulating a disclosed compounded composition.

In an aspect, a method of making a compounded composition can comprise encapsulating a compounded composition.

In an aspect, a disclosed method can comprise sterilizing a compounded composition.

All publications mentioned herein are incorporated herein by reference to disclose and describe the methods and/or materials in connection with which the publications are cited. The publications discussed herein are provided solely for their disclosure prior to the filing date of the present application. Nothing herein is to be construed as an admission that the present invention is not entitled to antedate such publication by virtue of prior invention. Further, the dates of publication provided herein can be different from the actual publication dates, which can require independent confirmation.

D. Expected Efficacy Of Various Anti-Infective Agents

Table 1 shows the expected efficacy of anti-fungal agents against various fungi.

Tables 2 and 3 show the expected efficacy of anti-bacterial agents against various bacteria.

TABLE 1

| 1. EFFICACY OF VARIOUS ANTIFUNGAL AGENTS | | | | | |
|---|---|---|---|---|---|
| | Fluconazole | Itraconazole | Voriconazole | Amphotericin | Nystatin |
| *Aspergillus flavus* | yes | yes | yes | yes | |
| *Aspergillus fumigatus* | yes | yes | yes | yes | |
| *Aspergillus niger* | | | yes | yes | |
| *Aspergillus terreus* | | | yes | yes | |
| *Blastomyces dermatitidis* | yes | yes | | yes | |
| *Candida* species | yes | yes | yes | yes | yes |
| *Coccidioides immitis* | yes | yes | | yes | |
| *Cryptococcus neoformans* | yes | yes | | yes | |
| *Fusarium* species | | | yes | | |
| *Histoplasma capsulatum* | yes | | | yes | |
| *Histoplasma duboisii* | | yes | | | |
| *Leishmania donovani* | | | | yes | |
| *Leishmania infantum* | | | | yes | |
| *Paracoccidioides brasiliensis* | | yes | | yes | |
| *Scedosporium apiospermum* | | | yes | | |
| *Sporothrix schenckii* | | yes | | | |
| *Trichophyton mentagrophytes* | | yes | | | |
| *Trichophyton rubrum* | | yes | | | |

TABLE 2

| 2. EFFICACY OF VARIOUS ANTIBIOTIC AGENTS | | | | | | |
|---|---|---|---|---|---|---|
| | Gram | Bactroban | Ceftriaxone | Vancomycin | Colistimethate | Ciprofloxacin |
| *Bacteroides fragilis* | anaer | | yes | no | no | no |
| *Clostridium difficile* | anaer | | no | yes | no | no |
| *Clostridium perfringens* | anaer | no | yes | no | | |
| *Chlamydia pneumoniae* | n/a | | no | no | no | yes |
| *Chlamydia psittaci* | n/a | | no | no | no | |
| *Chlamydia trachomatis* | n/a | | no | no | no | |
| *Mycoplasma pneumoniae* | n/a | | no | no | no | yes |

TABLE 2-continued

2. EFFICACY OF VARIOUS ANTIBIOTIC AGENTS

| | Gram | Bactroban | Ceftriaxone | Vancomycin | Colistimethate | Ciprofloxacin |
|---|---|---|---|---|---|---|
| *Acinetobacter baumannii* | neg | no | no | no | ± | ± |
| *Acinetobacter calcoaceticus* | neg | no | no | no | ± | ± |
| *Acinetobacter lwoffii* | neg | no | no | no | ± | ± |
| *Bartonella bacilliformis* | neg | no | ± | no | | yes |
| *Bordetella pertussis* | neg | no | no | no | no | ± |
| *Brucella species* | neg | no | ± | no | no | ± |
| *Campylobacter jejuni* | neg | no | no | no | | yes |
| *Citrobacter diversus* | neg | no | yes | no | | yes |
| *Citrobacter freundii* | neg | no | yes | no | | yes |
| *Enterobacter aerogenes* | neg | no | yes | no | yes | yes |
| *Enterobacter cloacae* | neg | no | yes | no | yes | yes |
| *Enterobacter sakazakii* | neg | no | yes | no | yes | |
| *Escherichia coli* | neg | no | yes | no | yes | yes |
| *Francisella tularensis* | neg | no | no | no | | yes |
| *Haemophilus ducreyi* | neg | no | yes | no | | |
| *Haemophilus influenzae* | neg | no | yes | no | | yes |
| *Haemophilus parainfluenzae* | neg | | yes | no | no | yes |
| *Klebsiella* (*Calymmato-bacterium*) *granulomatis* | neg | no | yes | no | yes | |
| *Klebsiella oxytoca* | neg | no | yes | no | yes | yes |
| *Klebsiella pneumoniae* | neg | no | yes | no | yes | yes |
| *Legionella pneumophila* | neg | no | no | no | no | yes |
| *Moraxella catarrhalis* | neg | no | yes | no | no | yes |
| *Morganella morganii* | neg | no | yes | no | | yes |
| *Neisseria gonorrhoeae* | neg | no | yes | no | no | yes |
| *Neisseria meningitidis* | neg | no | yes | no | no | yes |
| *Proteus mirabilis* | neg | no | yes | no | no | yes |
| *Proteus vulgaris* | neg | no | yes | no | no | yes |
| *Providencia rettgeri* | neg | no | yes | no | no | yes |
| *Providencia stuartii* | neg | no | yes | no | no | yes |
| *Pseudomonas aeruginosa* | neg | no | no | no | yes | yes |
| *Pseudomonas fluorescens* | neg | no | ± | no | yes | yes |
| *Rickettsiae* | neg | no | no | no | | yes |
| *Salmonella typhi* | neg | no | yes | no | | yes |
| *Serratia marcescens* | neg | no | yes | no | no | yes |
| *Shigella boydii* | neg | no | yes | no | | yes |
| *Shigella dysenteriae* | neg | no | yes | no | | yes |
| *Shigella flexneri* | neg | no | yes | no | | yes |
| *Shigella sonnei* | neg | no | yes | no | | yes |
| *Vibrio cholerae* | neg | no | no | no | no | yes |
| *Yersinia pestis* | neg | no | no | no | | yes |
| *Corynebacterium jeikeium* | pos | no | no | yes | no | no |
| *Corynebacterium urealyticum* | pos | no | no | yes | no | ± |
| *Diphtheroids* | pos | | no | yes | no | |
| *Enterococcus faecalis* | pos | | no | yes | no | ± |
| *Enterococcus faecium* | pos | | no | yes, not VRE | no | no |
| Methicillin resistant *staph aureus* (MRSA) | pos | yes | no | yes | no | no |
| *Peptostreptococcus* | pos | | yes | yes | no | ± |
| *Staphylococcus aureus* (MSSA) | pos | yes | yes | yes | no | ± |
| *Staphylococcus epidermidis* | pos | | yes | yes | no | yes |
| *Streptococcus agalactiae* | pos | | yes | yes | no | ± |
| *Streptococcus pneumoniae* | pos | | yes | yes | no | ± |
| *Streptococcus pyogenes* | pos | yes | yes | yes | no | ± |
| Viridans group streptococci | pos | | yes | yes | no | ± |

TABLE 3

3. EFFICACY OF VARIOUS ANTIBIOTIC AGENTS

| | Levofloxacin | Tobramycin | Doxycycline | Azithromycin | Clindamycin | Sulfa/Trim |
|---|---|---|---|---|---|---|
| *Bacteroides fragilis* | no | no | ± | no | yes | no |
| *Clostridium difficile* | no | no | ± | no | ± | no |
| *Clostridium perfringens* | yes | no | | no | yes - partial | no |
| *Chlamydia pneumoniae* | yes | no | yes | yes | ± | no |
| *Chlamydia psittaci* | | no | yes | yes | no | no |
| *Chlamydia trachomatis* | | no | yes | yes | no | no |
| *Mycoplasma pneumoniae* | yes | no | ± | yes | no | no |
| *Acinetobacter baumannii* | ± | no | no | no | no | ± |
| *Acinetobacter calcoaceticus* | ± | no | ± | no | no | ± |

TABLE 3-continued

3. EFFICACY OF VARIOUS ANTIBIOTIC AGENTS

| | Levofloxacin | Tobramycin | Doxycycline | Azithromycin | Clindamycin | Sulfa/Trim |
|---|---|---|---|---|---|---|
| *Acinetobacter lwoffii* | ± | no | no | no | no | ± |
| *Bartonella bacilliformis* | yes | ± | yes | yes | no | yes |
| *Bordetella pertussis* | ± | no | | yes | no | yes |
| *Brucella species* | ± | ± | yes | no | no | yes |
| *Campylobacter jejuni* | yes | yes | yes | yes | no | no |
| *Citrobacter diversus* | yes | yes | no | no | no | no |
| *Citrobacter freundii* | yes | yes | no | no | no | no |
| *Enterobacter aerogenes* | yes | yes | ± | no | no | yes |
| *Enterobacter cloacae* | yes | yes | ± | no | no | yes |
| *Enterobacter sakazakii* | yes | yes | ± | no | no | no |
| *Escherichia coli* | yes | yes | ± | no | no | yes |
| *Francisella tularensis* | yes | ± | yes | no | no | no |
| *Haemophilus ducreyi* | | yes | yes | | | ± |
| *Haemophilus influenzae* | yes | yes | yes | yes | no | ± |
| *Haemophilus parainfluenzae* | yes | | yes | | no | no |
| *Klebsiella (Calymmatobacterium)* | | yes | yes | no | no | yes |
| *Klebsiella oxytoca* | yes | yes | ± | no | no | yes |
| *Klebsiella pneumoniae* | yes | yes | ± | no | no | yes |
| *Legionella pneumophila* | yes | no | yes | yes | no | no |
| *Moraxella catarrhalis* | yes | yes | yes | yes | no | yes |
| *Morganella morganii* | yes | ± | no | no | no | yes |
| *Neisseria gonorrhoeae* | yes | no | ± | ± | no | ± |
| *Neisseria meningitidis* | yes | no | yes | yes | no | yes |
| *Proteus mirabilis* | yes | yes | no | no | no | no |
| *Proteus vulgaris* | yes | yes | no | no | no | no |
| *Providencia rettgeri* | yes | ± | no | no | no | ± |
| *Providencia stuartii* | yes | ± | no | no | no | ± |
| *Pseudomonas aeruginosa* | yes | yes | no | no | no | no |
| *Pseudomonas fluorescens* | yes | yes | | no | no | ± |
| *Rickettsiae* | yes | | yes | yes | no | no |
| *Salmonella typhi* | yes | | ± | ± | no | ± |
| *Serratia marcescens* | yes | yes | no | no | no | ± |
| *Shigella boydii* | yes | yes | ± | ± | no | ± |
| *Shigella dysenteriae* | yes | yes | ± | ± | no | ± |
| *Shigella flexneri* | yes | yes | ± | ± | no | ± |
| *Shigella sonnei* | yes | yes | ± | ± | no | ± |
| *Vibrio cholerae* | yes | no | yes | yes | no | yes |
| *Yersinia pestis* | yes | yes | yes | ± | no | yes |
| *Corynebacterium jeikeium* | no | no | | no | | |
| *Corynebacterium urealyticum* | ± | no | ± | ± | | no |
| Diphtheroids | | no | | | | |
| *Enterococcus faecalis* | yes | no | no | no | no | no |
| *Enterococcus faecium* | no | no | no | no | no | ± |
| Methicillin resistant *staph aureus* (MRSA) | no | no | ± | no | no | yes |
| *Peptostreptococcus* | ± | no | ± | ± | yes | yes |
| *Staphylococcus aureus* (MSSA) | yes | no | ± | yes | yes | yes |
| *Staphylococcus epidermidis* | yes | no | yes | yes | yes | yes |
| *Streptococcus agalactiae* | yes | no | ± | yes | yes | yes |
| *Streptococcus pneumoniae* | yes | no | yes | yes | yes | yes |
| *Streptococcus pyogenes* | yes | no | ± | yes | yes | ± |
| Viridans group streptococci | yes | no | ± | ± | yes | yes |

What is claimed is:

1. A method of treating or preventing a fungal infection in a subject, the method comprising:
   (i) compounding a footbath treatment mixture comprising mixing a therapeutically effective dosing amount of powdered fluconazole, an excipient base powder comprising a blend of micronized xylitol and poloxamers, and water;
   (ii) agitating the footbath treatment mixture within a footbath using an agitator; and
   (iii) contacting the agitated footbath treatment mixture with at least a portion of one or both feet of a subject that are infected or suspected to be infected with a fungal infection.

2. The method of claim 1, wherein the fluconazole powder and excipient base powder are mixed with the water in a ratio from about 1:60 to about 1:3 fluconazole powder to excipient base powder.

3. The method of claim 2, wherein the ratio is about 1:15.

4. The method of claim 1, wherein the method comprises repeating steps (i)-(iii) daily.

5. The method of claim 1, wherein the method further comprises heating the footbath treatment mixture contacting the at least a portion of one or both feet of the subject with the heated footbath treatment mixture.

6. The method of claim 1, wherein compounding the treatment mixture further comprises mixing one or more additional anti-infective agents with the fluconazole powder, excipient base powder, and water.

7. The method of claim 6, wherein the additional anti-infective agent comprises an anti-bacterial agent.

8. The method of claim 1, wherein the method further comprises administering to the subject an oral pharmaceutical composition comprising an anti-infective agent.

* * * * *